United States Patent
Yap et al.

(10) Patent No.: US 12,409,248 B2
(45) Date of Patent: Sep. 9, 2025

(54) HAEMOSTATIC DEVICE, HAEMOSTATIC COATING DISPERSION AND HYDROPHOBIC SURFACE

(71) Applicants: National University of Singapore, Singapore (SG); ETH Zurich, Zurich (CH)

(72) Inventors: Choon Hwai Yap, London (GB); Zhe Li, Singapore (SG); Dimosthenis Poulikakos, Zurich (CH); Athanasios Milionis, Zurich (CH)

(73) Assignees: ETH Zurich (CH); National University of Singapore, Singapore (SG)

( * ) Notice: Subject to any disclaimer, the term of this patent is extended or adjusted under 35 U.S.C. 154(b) by 603 days.

(21) Appl. No.: 17/765,715

(22) PCT Filed: Jun. 15, 2020

(86) PCT No.: PCT/SG2020/050336
§ 371 (c)(1),
(2) Date: Mar. 31, 2022

(87) PCT Pub. No.: WO2021/066739
PCT Pub. Date: Apr. 8, 2021

(65) Prior Publication Data
US 2022/0339316 A1    Oct. 27, 2022

(30) Foreign Application Priority Data
Oct. 4, 2019    (SG) .......................... 10201909296Q

(51) Int. Cl.
*A61L 15/52*    (2006.01)
*C08L 27/18*    (2006.01)
(Continued)

(52) U.S. Cl.
CPC ............... *A61L 15/52* (2013.01); *C08L 27/18* (2013.01); *C08L 83/04* (2013.01); *C08L 91/06* (2013.01);
(Continued)

(58) Field of Classification Search
CPC .. A61L 2400/12; A61L 2400/04; A61L 15/52; C08L 91/06; C08L 83/04; C08L 27/18
See application file for complete search history.

(56) References Cited

FOREIGN PATENT DOCUMENTS

| | | | |
|---|---|---|---|
| EP | 2210921 A1 | 7/2010 | |
| WO | WO-2009073854 A1 * | 6/2009 | ......... A61B 17/0057 |

OTHER PUBLICATIONS

The International Search Report and The Written Opinion of the International Searching Authority for PCT/SG2020/050336, Date of Mailing: Sep. 28, 2020.
(Continued)

*Primary Examiner* — Jacqueline F Stephens
(74) *Attorney, Agent, or Firm* — Botos Churchill IP Law LLP

(57) ABSTRACT

Described is a haemostatic device comprising a substrate and a surface formed on the substrate. The surface comprises at least one of micro- and nano-sized materials, the materials being partially embedded in a base, the surface substantially preventing wetting of the substrate. An embodiment of the device is carbon nano fibres embedded partially in a PDMS or PTFE base, on a substrate.

18 Claims, 20 Drawing Sheets

(51) Int. Cl.
*C08L 83/04* (2006.01)
*C08L 91/06* (2006.01)

(52) U.S. Cl.
CPC ....... *A61L 2400/04* (2013.01); *A61L 2400/12* (2013.01)

(56) References Cited

OTHER PUBLICATIONS

Das, et al., "Superhydrophobic and Conductive Carbon Nanofiber/PTFE Composite Coatings for EMI Shielding", Journal of Colloid and Interface Science, 2010, vol. 353, No. 1, pp. 311-315.

Li, et al., "Superhydrophobic Hemostatic Nanofiber Composites for Fast Clotting and Minimal Adhesion", Nature Communications, 2019, vol. 10, No. 5562, pp. 1-11.

Sasaki, et al., "Asymmetric Superhydrophobic/Superhydrophilic Cotton Fabrics Designed by Spraying Polymer and Nanoparticles", ACS Applied Materials & Interfaces, 2015, vol. 8, No. 1, pp. 651-659.

\* cited by examiner

HAEMOSTATIC DEVICE, HAEMOSTATIC COATING DISPERSION AND HYDROPHOBIC SURFACE

CROSS-REFERENCE TO RELATED APPLICATIONS

The present application is a national phase entry under 35 U.S.C. § 371 of International Application No. PCT/SG2020/050336, Jun. 15, 2020, published as International Publication No. WO 2021/066739 A1, which claims the benefit of the filing date of Singapore Patent Application No. 10201909296Q, filed Oct. 4, 2019, the disclosures of which are hereby incorporated by reference.

TECHNICAL FIELD

The present invention relates to a haemostatic coating dispersion, a hydrophobic surface formed using the haemostatic coating dispersion and a haemostatic device. The present invention relates to, but is not limited to, haemostatic patches for wound treatment.

BACKGROUND

Uncontrolled haemorrhage and wound infection are leading causes of death in the medical field of wound care. Improperly dressed wounds will prolong healing time and impose a high infection risk, leading to significantly increased mortality and economic burden. Haemostatic materials are consequently of great importance in medicine, in the successful repair and treatment of wounds.

Their successful implementation depends on two generally competing attributes: a) achieving blood coagulation rapidly, before significant blood loss, and b) enabling subsequent facile wound-dressing removal, without clot tears and secondary bleeding. The conventional method to deal with bleeding is mechanically pressing the wound with a cotton gauze. Cotton gauze unavoidably absorbs blood and causes unnecessary blood loss and gauze adhesion onto the wound. Blood absorbed in the gauze forms a solid clot-gauze composite, forced peeling of which often tears the wound and causes secondary bleeding and pain. This makes it difficult to replace the old wound dressing without causing secondary infections or haemorrhage, in procedures ranging from common wounds to surgery, and to the extreme case of haemophilic patients, where excessive bleeding will occur before coagulation.

To deal with these problems, active clotting agents (chitosan or kaolin) have been adopted into haemostatic materials, to reduce bleeding by expediting the coagulation process. However, such agents employ free micro-particles that may cause micro-thrombosis if they enter the vascular system, and can thus become a safety threat.

Recently, superhydrophobic (SHP) or superhydrophilic materials have been proposed for haemostatic purposes. A super-hydrophilic material (graphene sponge) is reported to absorb water from the blood quickly, forming a dense layer of blood cells and platelets, thus promoting coagulation. Hydrophilic haemostatic material can also be prepared by spray coating β-chitosan on a porous nanofiber mat, and the hydrophilic β-chitosan coating can increase blood wettability and thus enhance clotting. Alternatively, a SHP coating can be applied on the back of the normal superhydrophilic gauze as an impervious layer to prevent blood loss through the gauze. However, the core functionality of these approaches is still either based on a blood-absorbing haemostatic material (superhydrophilic) that does not minimize blood loss and secondary bleeding or a blood-repelling (superhaemophobic) material that simply repels blood but does not actively trigger clotting. Therefore, the aforementioned two key challenges on wound management still remain poorly addressed.

It is desirable that a device or material be provided to overcome or ameliorate at least one of the above-described problems, or at least to provide a useful alternative.

SUMMARY

Described herein is a strategy for achieving haemostasis by designing a SHP and blood-repelling surface that simultaneously achieves fast clotting with no blood loss, while also providing an anti-bacterial property and facilitating clot self-detachment.

The non-wetting feature of the SHP haemostatic surface can withstand substantial blood pressure and help reduce blood loss and bacteria attachment. As shown in investigations described with reference to the figures, carbon nanofibers (CNFs) immobilized on this surface can promote fast fibrin growth and thus clotting. Due to the presence of micro-air pockets within the blood-substrate contact area, there is minimal contact between the clot and the SHP CNF patch, leading to natural clot detachment after clot maturation and shrinkage. This reduces the peeling tension required to peel off the patch by about 1~2 orders of magnitude compared with a normal hydrophilic gauze or commercial haemostatic products. These features have been verified in vitro and in vivo, demonstrating the effectiveness of this strategy for designing haemostatic patch materials.

Described herein is a haemostatic device comprising:
a substrate; and
a surface formed on the substrate, the surface comprising at least one of micro- and nano-sized materials, the materials being partially embedded in a base, the surface substantially preventing wetting of the substrate. The surface may also be referred to as a coating. In some embodiments, the surface may be composed of the materials.

The materials may be hydrophobic. The materials may comprise hydrophobic nanofibers immobilized in the base.

The surface may have random surface morphology to obtain a water contact angle of at least 130°.

The surface morphology may entrain air pockets between the surface and a liquid coming into contact with the surface.

The haemostatic device may be one of a wound dressing, catheter-based stent, coil or graft—e.g. a medical patch with the surface formed on a cotton, synthetic fabric or polymeric membrane.

Also disclosed herein is a haemostatic coating dispersion comprising at least one of micro- and nano-sized materials, and a base (e.g. organic matrix) in a dispersion. The coating dispersion is for depositing on a substrate to form a hydrophobic surface comprising the micro/nano-materials partially embedded in the base. The obtained surface is substantially preventing wetting of the substrate.

The micro/nano-materials may be hydrophobic when at least partially embedded. These materials may comprise nanofibers immobilized in the base on formation of the surface. The nanofibers may be carbon nanofibers. The surface morphology may entrain air pockets between the surface and a liquid coming into contact with the surface.

The surface, once formed, may have a random surface morphology comprising micro-roughness and/or nano-roughness. The materials may comprise nanofibers having a diameter ranging from about 5 nm to 1 micron or microstructures having a diameter from about 1 µm to 200 µm. The materials may have a length of about 5 to 500 µm.

The base may be hydrophobic. The base may be an organic or polymeric matrix. The matrix may be at least one of polytetrafluoroethylene (PTFE), beeswax and polydimethylsiloxane (PDMS), or other biocompatible polymers capable of immobilizing the nanofibers.

Also disclosed herein is a hydrophobic surface formed by applying the haemostatic coating dispersion described above.

Advantageously, embodiments of the present invention overcome issues in the prior art relating to excessive blood loss during the period that the clot is forming and/or strong clot adhesion on the haemostatic dressing that causes pain, secondary bleeding, and possible infection during the wound-dressing removal.

Advantageously, embodiments of the present invention provide a haemostatic coating and device that can achieve (1) fast clotting, (2) clotting without blood loss, (3) clot self-detachment after clot maturation or solidification, and (4) minimize the adhesion of bacteria.

Advantageously, the haemostatic coating/device is superhydrophobic, providing enhanced repelling of water-based fluids such as blood. The present coating/device will thus reduce blood loss, as it repels blood to contain or restrict it within the wound. Moreover, the coating provides a non-wetting feature that can eliminate blood infiltration into the haemostatic material, thus preventing unnecessary blood loss. The non-wetting feature remains under high pressure of up to 300 mmHg, and thus will make the superhydrophobic haemostatic coating capable of dealing with artery bleeding. Moreover, the non-wetting property of the superhydrophobic CNF coating can prevent blood loss at the wound site by repelling blood and keeping blood within the wound. Blood will not penetrate through the material. This reduces blood loss. The coating is also capable of triggering fast clotting which can narrow the time window for bleeding, thus reducing blood loss during coagulation.

Advantageously, bacteria cannot attach to the coating easily. The anti-bacterial property can help to maintain the sterility of the haemostatic bandage and prevent wound infection.

Advantageously, the superhydrophobic haemostatic bandage or dressing or gauze can be easily peeled off from the clotted wound, without tearing the wound and causing secondary bleeding. In some cases, it facilitates self-detachment of the clot—e.g. during maturation and shrinkage.

Advantageously, the device is safe. Carbon nanofibers are immobilized onto the dressing or gauze by a biocompatible polymer. The immobilized carbon nanofibers would thus not enter the blood stream.

BRIEF DESCRIPTION OF THE DRAWINGS

Embodiments of the present invention will now be described, by way of non-limiting example, with reference to the drawings in which:

FIG. 3 shows the effect of different CNF nano-composite coatings on hydrophobicity and surface morphology, in which:

FIG. 3a shows the effect of concentrations on water contact angle, roll-off angle, and blood contact angle;

FIG. 3b shows SEM images of the hydrophobic surfaces HP #1 and HP #2; and

FIG. 3c shows SEM images of superhydrophobic nano-composite CNF surfaces;

FIG. 4 shows photographs of fibrin fibre generation on SHP CNF surfaces, in which:

FIG. 4a is a scanning electron microscope (SEM) image of the SHP CNF/PTFE Ti surface and a water droplet sitting on the surface, demonstrating excellent superhydrophobicity—scale is 10 µm;

FIG. 4b shows long fibrin fibres generated at the receding side of a 10 µl EDTA PPP droplet;

FIG. 4c illustrates a touch-lift test of a PPP droplet on the CNF surface, showing fibre generation upon EDTA PPP-substrate separation; and FIGS. 4d to 4g show close-up sequential frames of fibre generation and fracture during rolling down motion of the EDTA PPP droplet (20 µl), with FIG. 4e showing visible fibrin fibre footprints left on the CNF surface after the PPP sliding test;

FIG. 6 provides a schematic and photos of fibrin fibres generating on the superhydrophobic CNF/PTFE Ti surface after EDTA blood/plasma sliding, in which:

FIG. 6a illustrates blood/plasma sliding;

FIGS. 6b and 6c are optical images showing fibrin fibres left on the surface after PPP or blood sliding, and visible fibrin fibre footprints left on the CNF surface after sliding tests;

FIG. 6d provides SEM images of the CNF surface after blood sliding;

FIG. 6e provides a SEM image of the long, straight and aligned fibrin fibres left on the CNF surface after the PPP droplet rolled down the superhydrophobic CNF surface; and FIG. 6f is a SEM image of the long and straight fibrin fibres left on the CNF surface after the PPP droplet touch-lift test;

FIG. 8 shows citrated blood generated fibrin fibres on the superhydrophobic CNF/PTFE and CNF/PDMS surfaces, in which:

FIG. 8a shows a 20 µl water droplet sitting on the superhydrophobic CNF/PTFE Ti mesh;

FIG. 8b shows fibrin fibres generating at the receding side of a 40 µl citrated blood droplet on the superhydrophobic CNF Ti mesh:

FIG. 8c shows a 20 µl water droplet sitting on the superhydrophobic CNF/PDMS Ti surface; and FIG. 8d shows fibrin fibres generating at the receding side of a 20 µl citrated blood droplet on the superhydrophobic CNF/PDMS Ti surface;

FIG. 9a is an image showing no fibre observed for 20 µl EDTA blood or PPP droplets on the HP #1 sample (spray-coated with only PTFE);

FIG. 9b is an image showing no fibre observed for 20 µl blood or PPP droplets on the HP #2 sample (spray-coated with 0.2 wt % CNF in PTFE);

FIG. 9c shows SEM images of the HP #1 surface before and after PPP sliding, showing no straight fibrin fibres on the surface—scale bar is 10 µm;

FIG. 9d shows SEM images of the HP #2 surface before and after PPP sliding—scale bar is 10 µm;

FIG. 10 shows fibrin confirmation, in which:

FIG. 10a shows a fibrin ELISA test confirming the existence of fibrin on the superhydrophobic CNF surfaces after a sliding test by plasma (n, being in each case the number of measurements or repetitions, is 3);

FIG. 10b shows blood and PPP droplets with anti-thrombin (20 μl) quickly rolled down the superhydrophobic CNF/PTFE Ti surface at a small tilt angle without generating fibrin fibres at the receding side;

FIG. 10c illustrates the actual and nominal receding angles for blood or PPP droplets sliding down the superhydrophobic CNF surface with and without fibrin fibre generation; and FIG. 10d shows the dynamic contact angles for water droplets and blood or PPP droplets with and without anti-thrombin;

FIG. 11a schematically illustrates fibrin inhibition by anti-thrombin, argatroban;

FIGS. 11b and c are SEM images of the CNF surface after sliding by anti-thrombin blood and PPP, respectively, showing no aligned/straight fibrin fibre;

FIG. 11d shows no fibrin fibre was detected when a blood drop with anti-thrombin came into contact and was subsequently lifted from the superhydrophobic CNF surface;

FIG. 11e shows that swiping the CNF surface by PPP with anti-thrombin generated no fibrin fibres; and FIG. 11f is a SEM image of the CNF surface after PPP swiping test, showing no aligned/straight fibrin fibre;

FIG. 12a shows that, due to the droplet protrusion, the nominal receding angle $\theta_{r\_nom}$ is different from the actual receding angle $\theta_r$ for blood or PPP droplets on the superhydrophobic CNF surfaces;

FIG. 12b shows $\theta_{r\_nom}$, measured at the moment before catastrophic fibrin fibre fracture and droplet rolling down;

FIG. 12c shows the liquid-air interface;

FIG. 12d shows the smoothed liquid-air or liquid-substrate interface; and

FIGS. 12d to 12f show the position of D confirmed at the point on the circle where the pixel grey value had an abrupt change;

FIG. 13a shows a fibrous fibrin meshwork formed on the superhydrophobic CNF/PTFE Ti surface;

FIG. 13b illustrates an anti-bacterial capability, by comparing a substrate coated with the present coating side-by-side with an uncoated substrate;

FIG. 13c provides SEM images of the normal gauze and the CNF gauze;

FIG. 13d shows a relative haemoglobin absorbance RHA (t) plot, showing the fast clotting performance of the CNF gauze; and FIG. 13e schematically illustrates clotting without blood loss (n=3);

FIG. 14a provides optical images of the uncoated gauze;

FIG. 14b provides SEM images of the uncoated gauze; and

FIG. 14c provides SEM images of the gauze with clot, the clot and gauze being a solid piece;

FIG. 15a shows a clotting test by sandwiching 20 μl blood between two gauze samples (size: 15 mm by 15 mm);

FIG. 15b shows the nominal blood contact area of 20 μl blood on the uncoated white cotton gauze of FIG. 14a and a superhydrophobic CNF-coated gauze;

FIG. 15c shows clotting without blood loss;

FIG. 15d is a measurement of the maximum hydrostatic pressure that one layer of the CNF gauze (without an impervious membrane) can withstand before blood leakage; and FIG. 15e shows non-wetting of the CNF gauze by blood under high pressure;

FIG. 16 illustrates facile clot detachment, in which:

FIG. 16a—illustrates of fibrin fibres formation from blood on a superhydrophobic CNF surface;

FIG. 16b shows progress during clot maturation;

FIG. 16c is a SEM image of the micro-fibrin fibres adhered on the CNFs-coated cotton fibre after clot shrinkage (see also FIGS. 19a and 19b)—scale bar 25 μm;

FIG. 16d provides SEM images showing CNFs transferred onto clot after clot detachment, resulting in a smooth cotton fibre, and a hairy clot surface (see also FIG. 19c)—scale bar 50 μm;

FIG. 16e shows a clot self-peeling from a stiff CNF Ti mesh surface (see also FIGS. 18d to 18f); and FIG. 16f shows facile clot detachment;

FIG. 17 show facile clot detachment, in which:

FIG. 17a is a SEM image showing the aftermath of the clot contraction on the CNF gauze—scale bars are 50 μm;

FIG. 17b show some micro fibrin fibres remaining adhered on the CNF-coated cotton fibre after clot shrinkage—scale bars are 50 μm; and FIG. 17c provides SEM images of the clot surface in contact with the CNF gauze after clot detachment—scale bars are 50 μm;

FIG. 18 shows clot self-detachment on the stiff CNF/PTFE Ti mesh, in which:

FIG. 18a is a SEM of the pristine Ti mesh #60 before CNF coating;

FIGS. 18b and 18c are SEM images of the Ti mesh after coating with superhydrophobic CNF (thickness of the CNF layer was approximately 20 μm);

FIG. 18d shows clot contraction on the CNF Ti mesh;

FIG. 18e shows clot self-detached from the CNF Ti mesh; and

FIG. 18f is a photograph of the hairy area on the clot, which was in contact with CNF;

FIG. 19 illustrates in vivo animal experiments, in which:

FIG. 19a shows plaster-like gauzes were patched onto incisions on the back of a rat (see also FIGS. 21a to 21c);

FIG. 19b shows peeling of the gauze at 3 min to measure the blood loss;

FIG. 19c shows peeling of the gauze at about 2 h to measure the peeling force (FIGS. 21a to 21i);

FIG. 19d shows that the CNF gauze minimized blood loss (n=6)—shown as mean±SD, the error bar representing SD and individual data points in d and e are represented by black stars;

FIG. 19e confirms the peeling force for the CNF gauze was significantly smaller than that for the normal gauze (n=5)—shown as mean±SD, the error bar representing SD and individual data points in d and e are represented by black indicia;

FIG. 19f provides SEM images of the area in contact with blood on the CNF gauze in FIG. 19c—CNF residuals after clot detachment were observed on cotton fibres—scale bar is 1119 µm;

FIG. 19g provides SEM images of the area not in contact with blood on the CNF gauze in FIG. 19c, where cotton fibres were densely coated with CNFs—scale bar is 15 µm;

FIG. 19h provides SEM images of the peeled normal gauze in FIG. 19c—scale bar is 100 µm; and FIG. 19i is a schematic of the haemostatic CNF gauze/plaster for wound treatment;

FIG. 20 shows the comparison of the clot peeling tension of the CNF gauze with commercial products, in which:

FIG. 20a shows the commercial products used for comparison;

FIG. 20b shows the procedures used to measure the clot peeling force; and

FIG. 20c summarizes the water contact angle and the clot peeling tension for different samples;

FIG. 21 relates to in vivo experimentation, in which:

FIG. 21a shows the design of the plaster-like gauze;

FIG. 21b is a photograph of the prepared plaster-like CNF gauze and the control normal gauze;

FIG. 21c is a schematic of the application of gauze onto the wound made on the back of an anaesthetised and shaved rat;

FIG. 21d shows the CNF gauze and the control gauze applied onto the wounds on back of the rat;

FIG. 21e provides a comparison between the CNF gauze and the normal gauze peeled at 3 minutes;

FIG. 21f shows the CNF gauze after peeling;

FIG. 21g schematically illustrates the gauze and control after trimming away the adhesive film around the gauze;

FIG. 21h illustrates the peeling force measurement process; and

FIG. 21i provides two typical peeling force versus time curves for the normal gauze and the CNF gauze, and the maximum peeling force was used for comparison (n=5);

FIG. 22 provides measurement of the clot peeling tension, in which:

FIG. 22a shows a clot formed by dispensing 20 µl blood onto the CNF gauze surface;

FIG. 22b shows a clot formed between two normal gauzes by dispensing 20 µl blood;

FIG. 22c shows a typical clot peeling force curve; and

FIG. 22d provides a measurement of the clot maximum width W for the calculation of the clot peeling tension $F_{max}/W$;

FIG. 23 shows the effects of CNF weight percentage on hydrophobicity and the fibrin fiber generation capability, in which:

FIG. 25 relates to in vivo skin compatibility testing, in which:

FIG. 25a shows the design of the prepared sample for test;

FIG. 25b shows four pieces of prepared samples were attached onto rat skin with hairs shaved; and FIG. 25c shows the haemostatic surface is skin compatible and does not cause skin irritation after contact with skin for 12 hours; and

DETAILED DESCRIPTION

Described with reference to the drawings are a hydrophobic surface, a haemostatic dispersion and a haemostatic device for achieving haemostasis. Some embodiments of these surfaces, dispersions and devices are directed to achieving both rapid blood coagulation before significant blood loss, and subsequent removal of facile wound-dressings without clot tears and secondary bleeding. These objectives are achieved via a superhydrophobic (SHP) surface with immobilized carbon nanofibers (CNFs).

CNFs are shown herein to promote quick fibrin growth and cause rapid clotting. Moreover, due to their superhydrophobic nature they severely limit blood wetting to prevent blood loss and drastically reduce bacteria attachment. Furthermore, minimal contact between the clot and the superhydrophobic CNF surface yields an unforced clot detachment after clot shrinkage.

These important attributes are verified in vitro and in vivo with rat experiments. The work set out below thereby demonstrates that this strategy for designing haemostatic patch materials has great potential.

Figure 1:
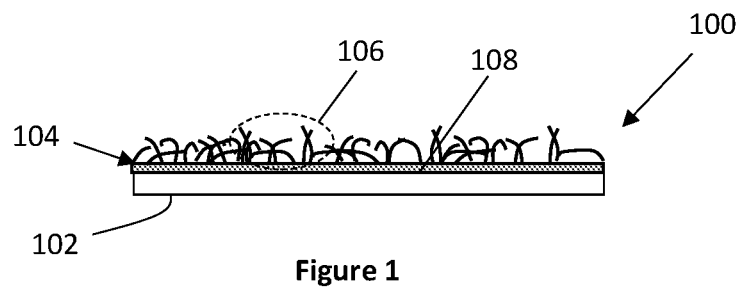
FIG. 1 illustrates a device in accordance with present teachings.

A haemostatic device 100 in accordance with present teachings, is shown in FIG. 1. The haemostatic device 100 includes a substrate 102 and a surface 104 formed on the substrate 102. The surface 104 includes materials 106 that are partially embedded in a base 108. The base 108 may be hydrophobic, though this is not essential since hydrophobic nanofibres will confer the necessary hydrophobicity on the device 100.

This partial embedding results in part of the materials 106 protruding from the base 108. The materials referred to herein may also be referred to as structures, if permitted by context. The protruding ends can give the surface 104 a random surface morphology. With appropriate formation of the surface 104 using micro-sized and/or nano-sized materials in accordance with the method below, random morphology can be used so the surface 104 can obtain a high water contact angle (WCA)—for example, some embodiments may achieve a WCA of at least 130°, where other embodiments may achieve a WCA lower than 130°. The random surface morphology will typically be one of microroughness and nano-roughness. The roughness will largely depend on the size of the materials 106 embedded in the base 108.

The surface morphology results in the creation of air pockets that entrain air when a liquid comes into contact with the surface 104. This entrainment of air prevents the liquid from wetting down the materials 106, and onto the base 108 or substrate 102.

The materials 106 are each a micro-sized or nano-sized material, through which the surface 104 substantially prevents wetting of the substrate 102. The materials 106, presently nanofibers or predominantly nanofibers, are hydrophobic. The materials may be formed from carbon or a non-carbon material such as polymeric fibre, silicon fibre or coated cellulose fibre.

To avoid displacement of the materials, which might otherwise create areas on the substrate 102 to which liquids may attach, the hydrophobic nanofibers 106 are immobilized in the base 108. This also largely prevents the materials from dislodging during use.

Figure 2:
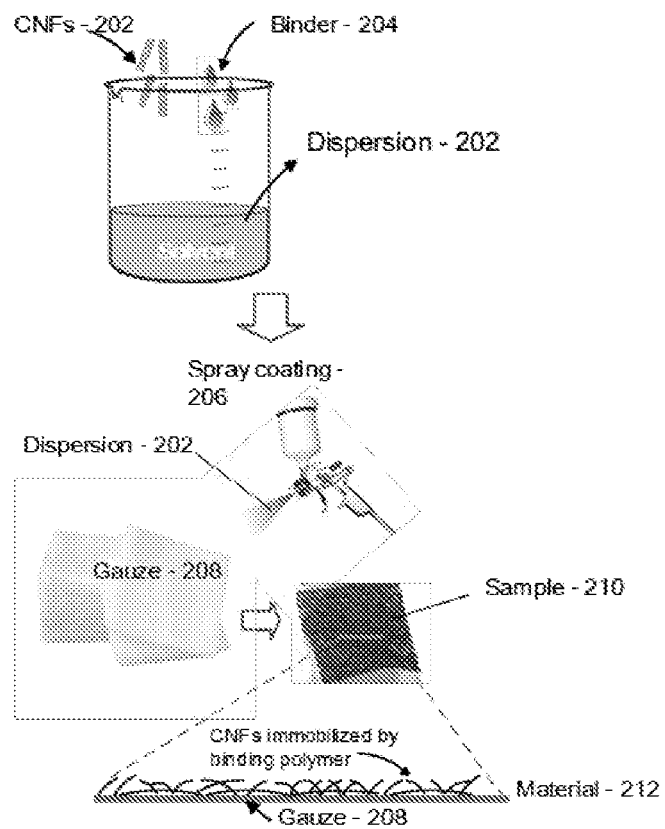
FIG. 2 schematically represents a method for forming the device of FIG. 1.

With reference to FIG. 2, the surface 104 can be formed by depositing a haemostatic coating dispersion 200 on the substrate 102. The haemostatic coating dispersion 200 includes micro-sized or nano-sized materials 202 and a base 204. The present surface 104 is a superhydrophobic carbon nanofiber (CNF) coating. In an experiment, CNFs of 98% purity, 100 nm diameter, 20-200 µm length, were pre-mixed with a biocompatible polymer capable of immobilising the CNFs, presently being polytetrafluoroethylene (PTFE) powder (1 µm particle size). In some embodiments, the CNF diameter may vary (e.g. between about 5 nm to 1,000 nm) and the length may similarly vary as needed (e.g. between about 5 µm to 500 µm). In other embodiments, a micro-sized material may be used having, for example, a diameter from about 1 µm to 200 µm. Polydimethylsiloxane (PDMS) was also trialled in place of PTFE, and other compounds such as beeswax, non-hydrophobic compounds and combinations thereof can provide similar properties. In accordance with embodiments herein, the case may be any compound capable of fixing the materials (e.g. nanofibres) onto the substrate in a manner that creates air pockets when the materials come into contact with fluids such as blood and PPP. The dispersion—i.e. materials 202 and base 204—were then applied on substrates via spray coating 206.

Figure 16:
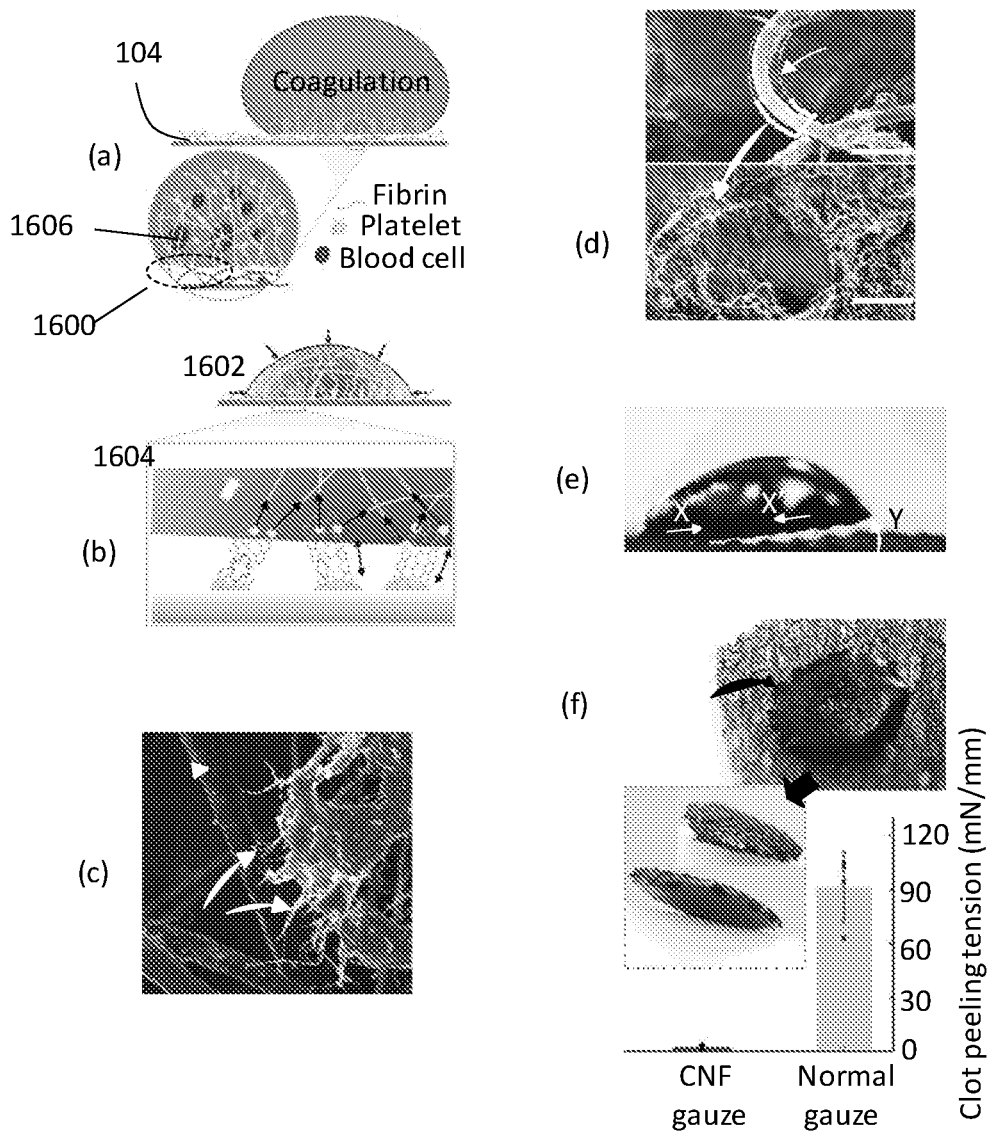
Figure 18:
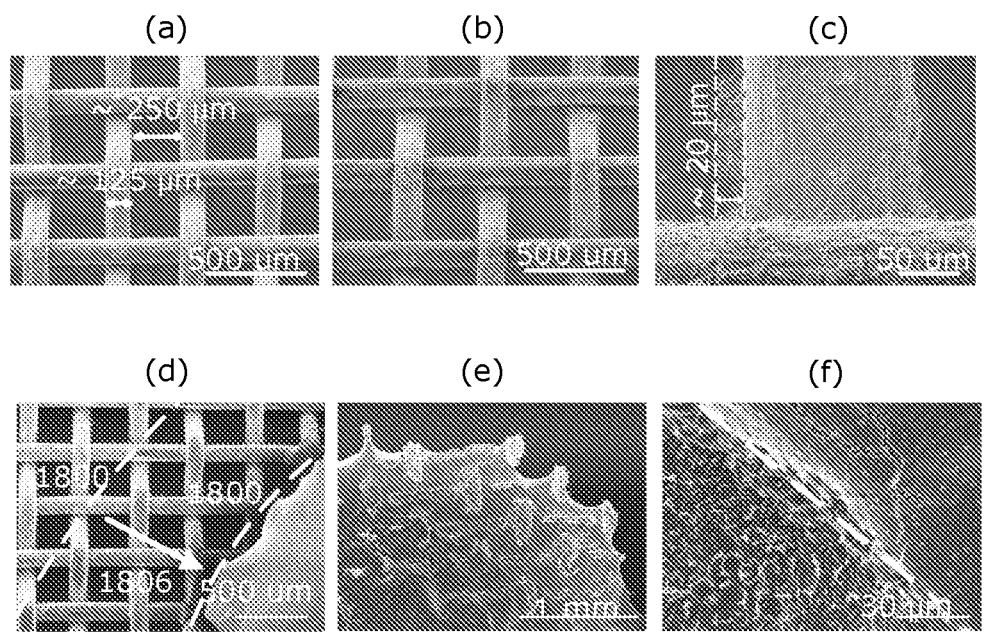

The substrates used were a flat Titanium (Ti) substrate (Ti6Al4V, 1 mm thick) though, in other embodiments, transparent glass slides (25 mm by 75 mm, 1.1 mm thick) may be appropriate. The Ti forms a mesh having a nominal aperture of 250 µm, and wire diameter of 125 µm. (see FIG. 18a, showing a SEM image of the pristine Ti mesh #60 before CNF coating, with a nominal aperture of about 250 µm and a wire diameter of about 125 µm). These substrates were ultrasonically cleaned (10 min) with acetone and isopropanol, and were further cleaned with oxygen plasma. Commercially available cotton woven gauze 208 (see FIGS. 16a and 16b) was also used as substrate—other substrates, such as fabrics, may also be used to, for example, create a flexible patch for conforming to various bodily surface.

Before spray coating, a CNF/PTFE or CNF/PDMS composite dispersion in dichloromethane was first prepared by mixing the CNF and dichloromethane dispersion with the PTFE and dichloromethane or PDMS and dichloromethane dispersion. The CNF and dichloromethane dispersion was prepared by dispersing CNFs in dichloromethane with a probe ultrasonicator for 1 min. The PTFE and dichloromethane or PDMS and dichloromethane dispersion was prepared by dispersing the PTFE powder or PDMS (pre-polymer to cross linker weight ratio 9:1) in dichloromethane under ultrasonication for 20 min. The CNF and dichloromethane dispersion was then mixed with the PTFE and dichloromethane or PDMS and dichloromethane dispersion, and sonicated for 10 min to prepare the CNF/PTFE or CNF/PDMS composite dispersion in dichloromethane. The composite dispersion was spray-coated onto sample substrates at a pressure of 430 kPa. The spray-coated CNF/PTFE sample 210 was baked for 30 min at 400° C. in a low oxygen environment to prevent oxidization. The CNF/PDMS sample was baked at 80° C. for 1 h. As the cotton could not withstand the high temperature (400° C.) for PTFE coating, the cotton gauze was coated with CNF/PDMS instead. The CNF/PTFE nanocomposite had a CNF to PTFE weight ratio of 1:9. The CNF/PDMS nanocomposite had a CNF to PDMS weight ratio of 1:2, whereas a higher concentration of PDMS would cause CNF agglomeration and result in significant coverage of the exposed CNF surface by PDMS. This would lead to roll-off angles (RAs) larger than 10°.

The effect of CNF concentration on superhydrophobicity was also investigated by spray coating low-concentration CNF on Ti substrates (HP #1: only PTFE; HP #2: 0.2 wt % CNF in PTFE) following the same protocol. This allowed a study of the weight ratios of binding/polymer material and their effect on hydrophobicity and clot-promotion. Hydrophobicity is characterized by the water contact angle (≥150°). Clot-promoting capability is tested by fiber fibrin generation at the receding side of the blood droplet as it is sliding/rolling on the CNF composite surface.

Figure 23A:
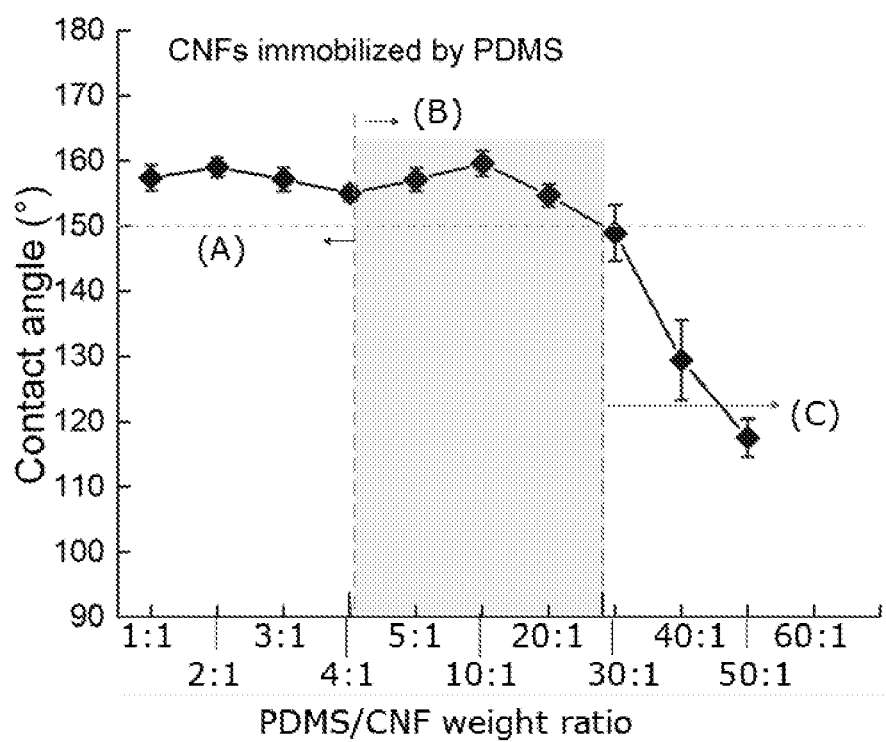
FIG. 23a shows the CNF/PDMS composite surface.
Figure 23B:
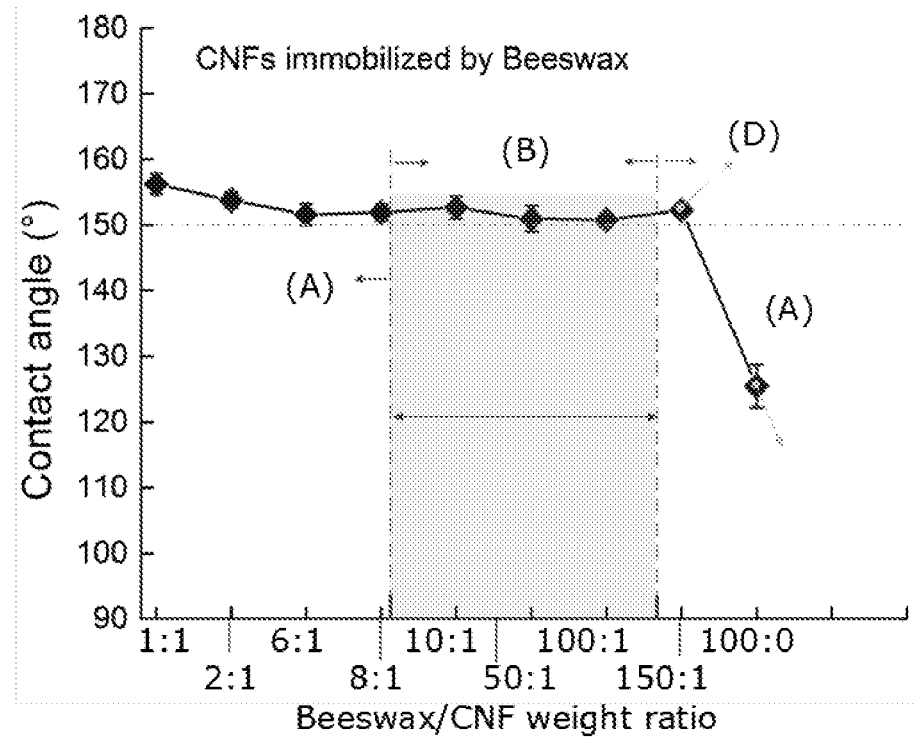
FIG. 23b shows a CNF/beeswax composite surface.

This investigation was conducted using two binding polymers/materials, PDMS and beeswax—results are shown in FIG. 23, comprising FIGS. 23a and 23b. Each graph is divided into three regions, (A), (B) and (C). Region (A) starts from the left-hand side and continues to $WP_{min}$, being the minimum desirable weight percentage ratio of PDMS or beeswax to CNFs. In Region (A) the CNFs were free or not sufficiently immobilized. CNFs were considered sufficiently immobilized for weight percentage ratios of PDMS or beeswax to CNFs, of at least $WP_{min}$. In region (B), extending from to $WP_{min}$ $WP_{max}$, CNFs were sufficiently immobilized and there was fibrin fibre generation. In FIG. 23(a), region (C) showed substantially no fibrin fibre generation. In FIG. 23(b), region (C) initially showed some fibrin fibre generation to point (D) but with free CNF and beeswax agglomerates, and thereafter fibrin fibre generation was inhibited. Accordingly, this investigation found the weight percentage of the binding polymer/material should be in a given range (that is, not smaller than a minimal value $WP_{Min}$, and not larger than a maximum value $WP_{max}$) to make the CNF composite surface both superhydrophobic and fibrin fibre generation-promoting. When the weight percentage is smaller than $WP_{min}$, CNFs are not sufficiently immobilized on the surface. Free CNFs will be observed floating on the water droplet, if one droplet is dispensed on the surface. When the weight percentage of the binding polymer/material is larger $WP_{max}$, the CNF composite surface will either not be superhydrophobic, be unable to promote fibrin fiber generation, or have some loosely attached CNF and binding material/polymer agglomerates.

As for the CNF/PDMS composites, the PDMS to CNF weight ratio should be in the range of 4:1 to 30:1, as shown in FIG. 23a. When the PDMS/CNF weight ratio is smaller than 4:1, free CNFs will be observed on the surface. When the PDMS/CNF weight ratio is larger than 30:1, the surface will not be superhydrophobic (contact angle smaller than 150°), will have strong adhesion to blood, and no fibrin fibre will generated at the receding side of the blood droplet.

As for the CNF/beeswax composites, the beeswax to CNF weight ratio should be in the range of 8:1 to 150:1. When the beeswax/CNF weight ratio is smaller than 8:1, free CNFs will be observed on the surface. When the beeswax/CNF weight ratio is higher than 150:1, the surface is still superhydrophobic, partially due to self-agglomeration of beeswax in the spray coating process (micro-beeswax particles could be observed on the spray coated beeswax surface), and also promotes fibrin fibre generation (due to the presence of CNF fibre). However, at this high beeswax weight ratio, spray-coating will generate some free CNF & beeswax agglomerate particles (that are loosely attached on the surface); these loose particles can be observed when a blood droplet is dispensed on the surface (FIG. 23b). Thus a high concentration of beeswax for CNF immobilization is not beneficial.

In FIG. 23 dichloromethane ($CH_2Cl_2$) was used as the carrier medium to dissolve/disperse PDMS, beeswax, and CNF. The carrier medium is used to evenly mix the binding polymer/material with the CNF. After spray coating, the carrier medium will evaporate. The carrier medium can be a single solvent, a mixture with a few different solvents, or a mixture with water. Solvents such as acetone, ethanol, toluene, hexane, acid solution, alkaline solution, and water that can dissolve/disperse the binding polymer/material and the CNF can also be used.

Relatedly, the results of the investigation into the effect on hydrophobicity and surface morphology of different carbon nanofibre (CNF) nano-composite coatings is shown in FIG.

3—particularly FIGS. 3a and 3b. FIG. 3a shows the water contact angle, roll-off angle, and blood contact angle on different superhydrophobic surfaces. Data in the bar graph are shown as mean±SD, and the error bar represents SD (the number of measurements n is 5). FIG. 3b shows SEM images of the hydrophobic surfaces HP #1 (301) and HP #2 (303). HP #1 refers to a hydrophobic Ti surface coated with only PTFE that has a water contact angle of 130.8±2.1°. HP #2 refers to a Ti surface coated with 0.2 wt % CNF in PTFE that has a water contact angle of 143.6±3.1°.

FIG. 3c provides SEM images of superhydrophobic nanocomposite CNF surfaces. The CNF/PTFE surface had a surface morphology similar to the CNF/PDMS surface. On the superhydrophobic CNF/PTFE and CNF/PDMS Ti surfaces, blood had a smaller contact angle than water (but still larger than) 150° due to the lower surface tension of blood. On the superhydrophobic CNF/PTFE Ti mesh surface, the contact angle could not be accurately measured due to the special mesh topography. On the hydrophobic surfaces (HP #1 and HP #2), the reduced surface roughness led to a smaller water contact angle.

To remove any loosely attached CNFs, samples were prepared and exposed to compressed $N_2$ gas from a spray gun (nozzle diameter: 0.8 mm; pressure: 430 kPa; sample to nozzle distance~15 cm) before testing to make sure there was no free CNF on the present material 212.

The result is a hydrophobic surface formed using a haemostatic dispersion. That hydrophobic surface may be used in a device such as device 100 shown in FIG. 1—the device 100 being, for example, a wound dressing, catheter-based stent, coil or graft, formed from a haemostatic dispersion.

Devices, in the form of wound dressings, formed according to the method described above were tested for fibrin formation, anti-bacterial properties, clotting and facile clot detachment. Fibrin 1102 is converted from fibrinogen 1100. Fibrinogen is a glycoprotein complex, made in the liver that circulates in the blood. During tissue and vascular injury, fibrinogen is converted enzymatically by thrombin 1104 to fibrin and then to a fibrin-based blood dot. Fibrin clots function primarily to occlude blood vessels to stop bleeding. Fibrin formation is therefore critical in wound healing and promoting its formation can reduce bleeding.

Figure 3:
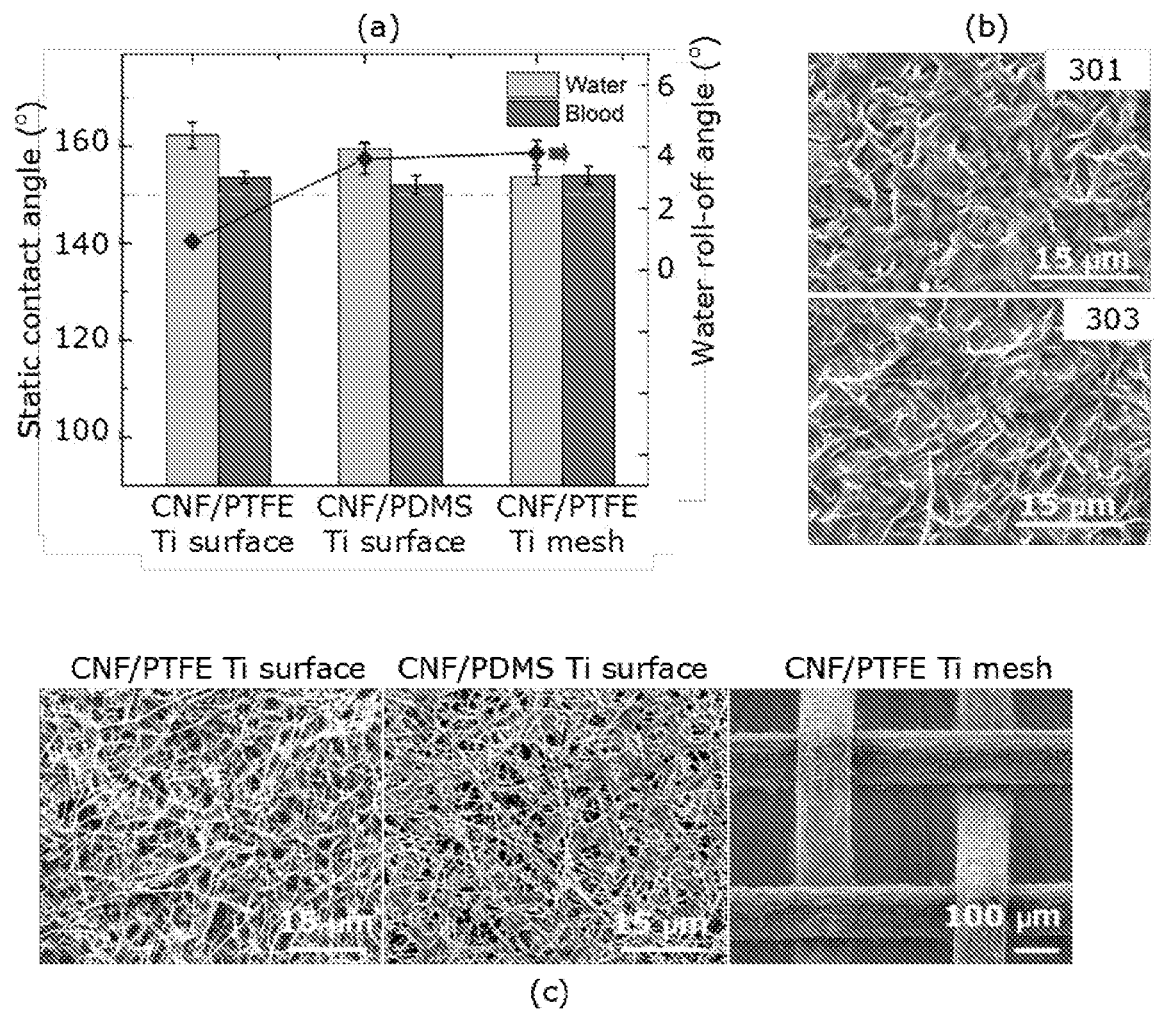

Referring firstly to results relating to fibrin fibre formation on superhydrophobic CNF surfaces: for effective haemostatic performance, the present SHP surface is designed first to be strongly blood-repellent and second to be capable of triggering fast coagulation upon blood contact. Being extremely blood repellent is achieved by spray coating a nanocomposite dispersion, such as that described above consisting of CNFs (diameter: 100 nm, length: 20-200 μm), and polytetrafluoroethylene (PTFE) or polydimethylsiloxane (PDMS), onto a substrate as shown in FIG. 3. Examples of the bases used are set out in Table 1.

TABLE 1

Superhydrophobic nanocomposite coatings

| Coating abbreviation | Substrate | Polymer matrix | CNF to polymer weight ratio |
|---|---|---|---|
| CNF/PTFE Ti | Ti plate | PTFE | 1:9 |
| CNF Ti mesh | Ti mesh #60 | PTFE | 1:9 |
| CNF/PDMS Ti | Ti plate | PDMS | 1:2 |
| CNF gauze | Cotton gauze | PDMS | 1:2 |

Figure 4:
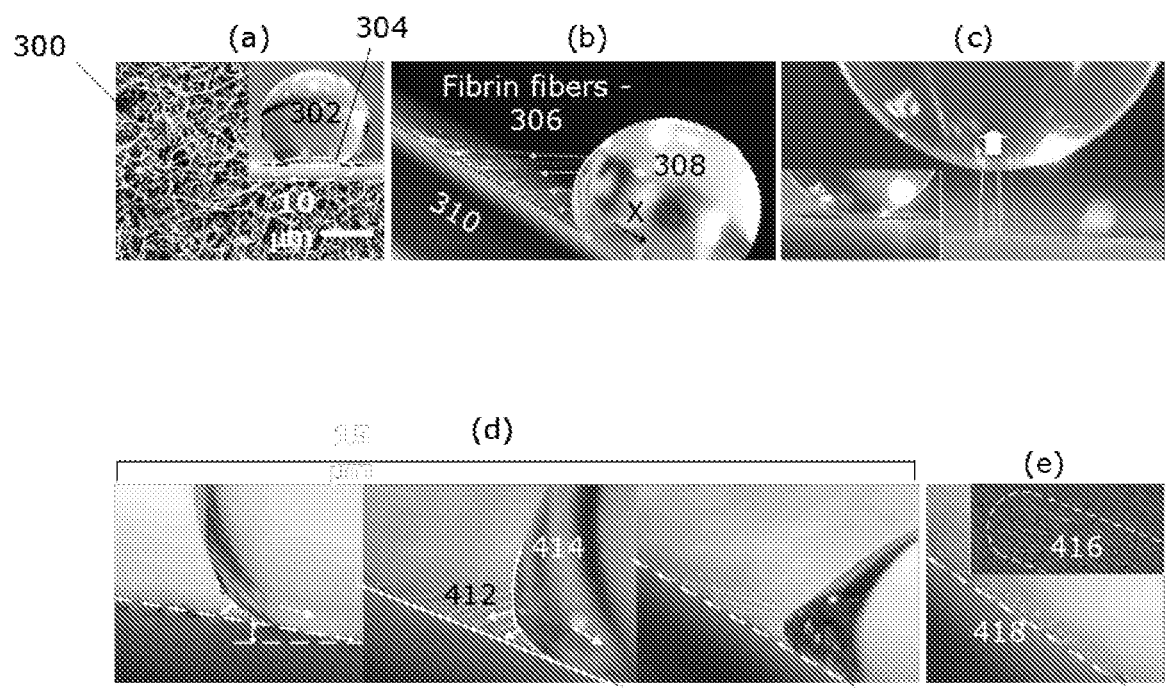

The surface generated by the above process has a dense layer of CNF network with micro/nano-roughness that is partially embedded in a hydrophobic polymer matrix (PTFE or PDMS). A photograph of the surface 300 is shown in FIG. 4a, with an inset photograph of a water droplet 302, showing a water contact angle of 162.5°, and air plastron (air pocket) region being indicated by reference numeral 304. Photographs of relevant actual experimental results are shown in FIG. 3c.

The use of hydrophobic base components, the micro/nano-scale topography from spray coating, and the morphology of the nanofibers collaboratively result in superhydrophobicity. The CNF/PTFE Ti surface had a water contact angle (WCA) of 162.1±2.9° (mean±SD) and a water roll-off angle (WRA) of about 1°, and the CNF/PDMS Ti surface had a WCA of 154.9±0.6° and a WRA of about 4°—see FIG. 3a.

The effect of CNF concentration on surface wetting was also investigated as shown in FIG. 3. Compared with water, blood has a smaller surface tension of 58 mN m$^{-1}$ (72 mN m$^{-1}$ for water) and a complex composition. However, the present SHP CNF surfaces could still repel it, with blood contact angles (CAs) of 153.6±1.4° for the CNF/PTFE Ti surface and 151.4±1.8° for the CNF/PDMS Ti surface (see FIG. 3a).

Figure 5:
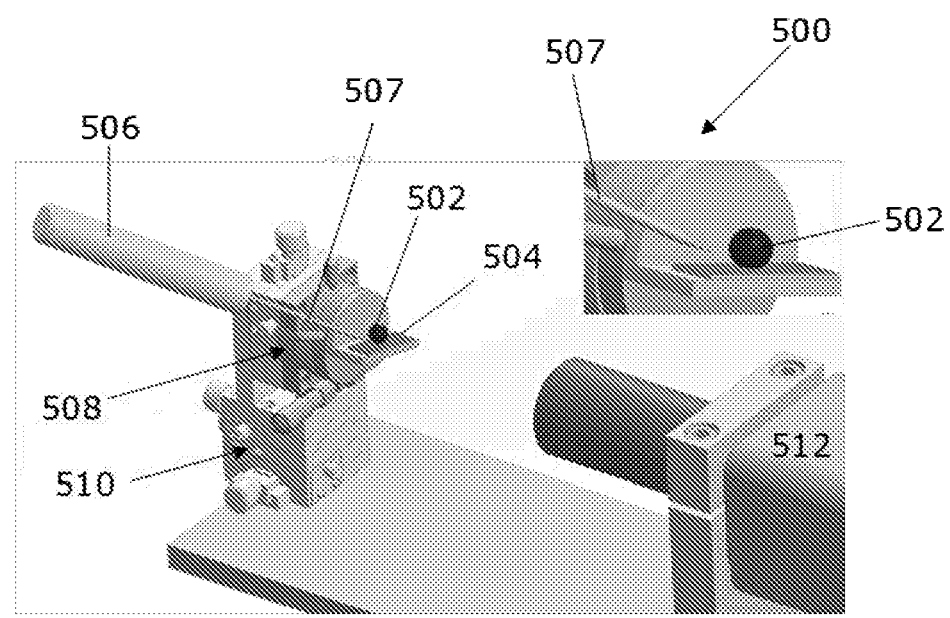
FIG. 5 schematically illustrates the setup used to visualize fibrin fibre generation.

Very interestingly and unexpectedly, it was observed that when blood or platelet poor plasma (PPP) with anticoagulant ethylenediaminetetraacetic acid (EDTA) or sodium citrate was brought into contact with the present SHP CNF surfaces, long straight fibres (later confirmed to be fibrin) formed rapidly. This was tested using the setup shown in FIG. 5, for visualizing fibrin fibres generation at the receding side of the blood/plasma droplet sliding down a superhydrophobic CNF surface. In order to visualize fibrin fibres during blood or PPP sliding, backlighting in a typical goniometer was avoided due to over-exposure, and a light source was projected at a proper angle from the side to make fibrin fibres visible. The setup 500 was used in conjunction with a blood/plasma droplet 502 on a SHP CNF surface 504 formed in accordance with present teachings. A light-emitting diode (LED) torch 506 emitted light 507 at a desired angle, onto the CNF surface 504. The CNF surface 504 was positioned on a stage assembly comprising a rotatable stage 508 and a translatable stage 510. Angles and fibrin formation, particularly during sliding tests, were observed by photographs captured using camera 512.

In the sliding test shown in FIG. 4b, abundant long fibres 306 were generating at the receding side of the plasma droplet 308 as it rolled in direction X down surface 310. These fibres 412 pulled the droplet 414 as shown in FIG. 4d, retarding its sliding motion, until a critical angle was reached, causing catastrophic fibre fracture and allowing the droplet to roll off quickly. After the first one or two fibres started to rupture, the remaining fibres could not hold the droplet weight and their rupturing occurred in the form of a rapid domino effect. After the PPP droplet rolled off, visible fibre footprints 416 were left on the surface 418 (FIG. 4e), in the form of straight and ordered fibres 600 on top of random CNFs 602 (FIG. 6e), aligning in the droplet rolling direction 604. The same was observed after blood droplet sliding (FIG. 6d). Similar observations were made in a slightly different test, the touch-lift test, where a PPP or blood droplet was brought onto the CNF surface for a brief contact and then retracted (contact duration~3 s; FIG. 4c), and fibrin fibre generation was also observed. Long and straight fibres (up to 300 μm) projecting outward from the contact centre were detected under scanning electron microscopy (see SEM image FIG. 6f).

Figure 6:
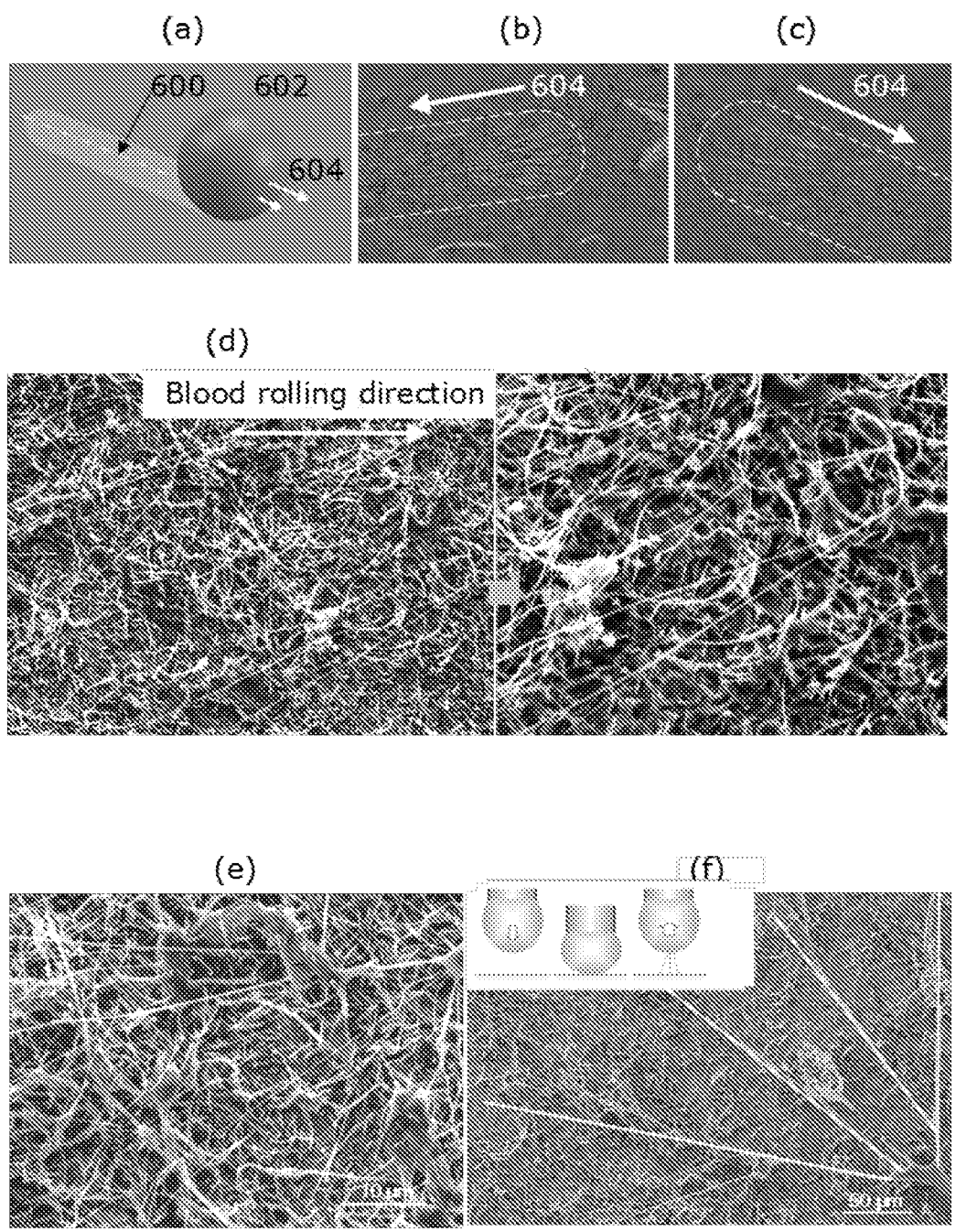

FIG. 6 provides images of fibrin fibres generating on the superhydrophobic CNF/PTFE Ti surface after EDTA blood/plasma sliding tests. FIG. 6a illustrates blood/plasma sliding. FIGS. 6b and 6c are optical images showing fibrin fibres left on the surface after PPP or blood sliding, and visible fibrin fibre footprints were left on the CNF surface after sliding tests. FIG. 6d provides SEM images of the CNF surface after blood sliding. Long, straight and aligned fibrin fibres can be observed on top of random CNFs. Arrows are used to highlight the aligned fibrin fibres. FIG. 6e is a SEM image of the long, straight and aligned fibrin fibres left on the CNF surface after the PPP droplet rolled down the superhydrophobic CNF surface. FIG. 6f is a SEM image of the long and straight fibrin fibres left on the CNF surface after the PPP droplet touch-lift test.

Figure 7:
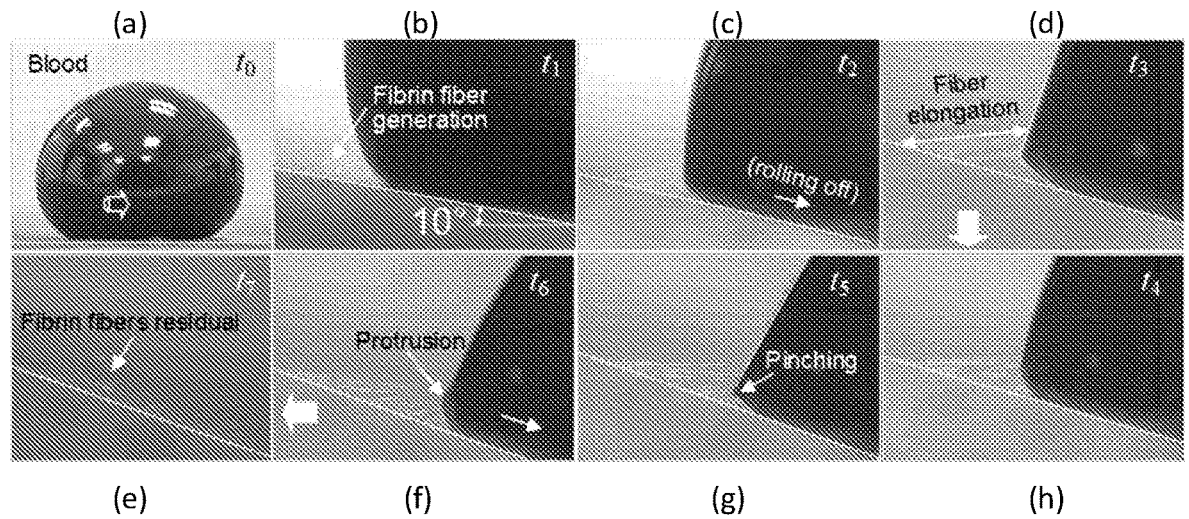
FIG. 7 comprises FIGS. 7a to 7h that show progressive stages in the development and severing of fibrin at the receding surface of a blood droplet during a roll-off test.
Figure 8:
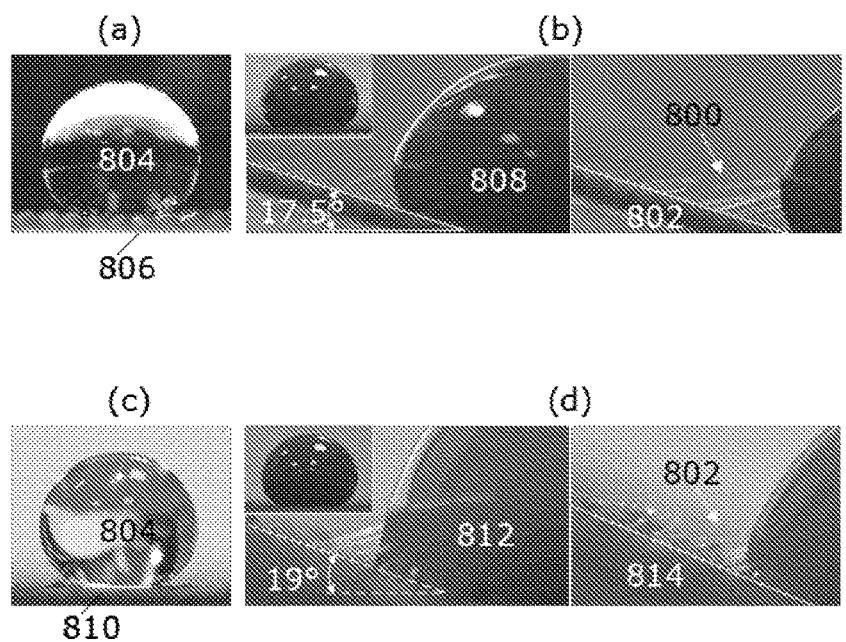
Figure 13:
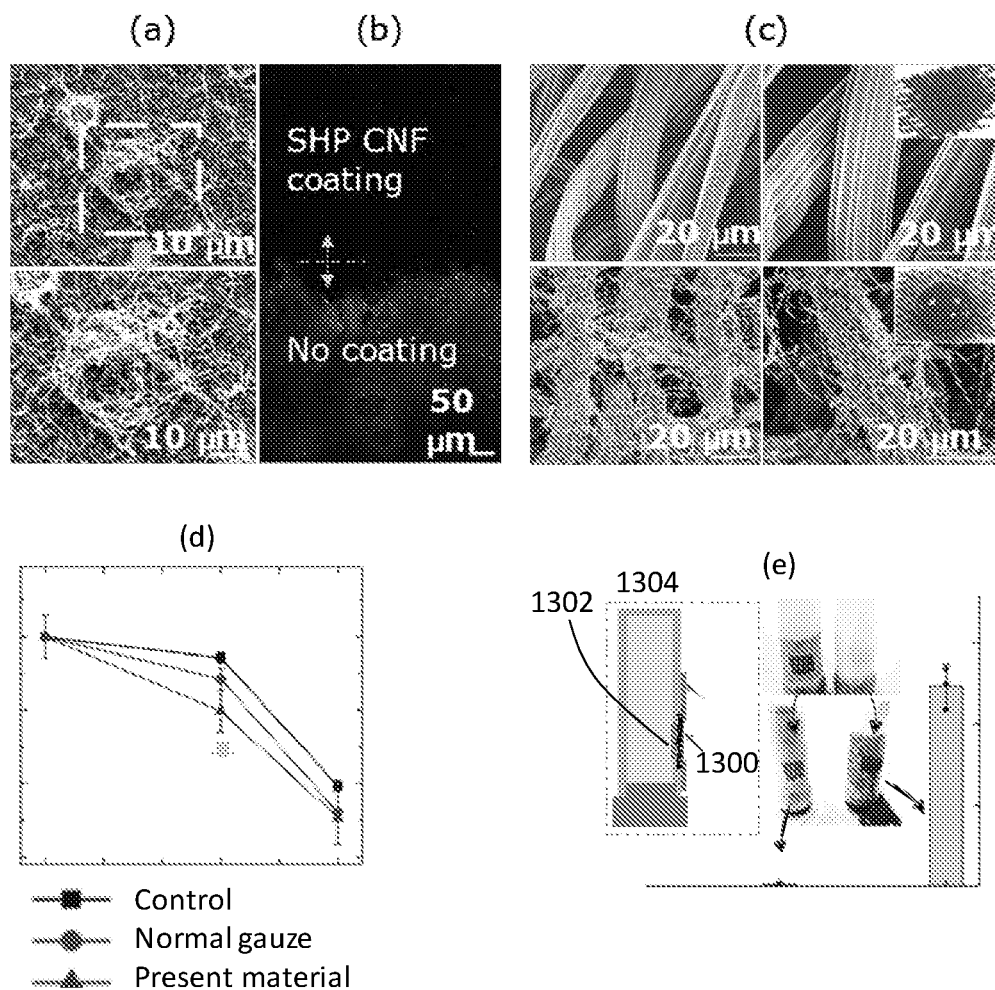
FIG. 13 illustrates anti-bacterial, rapid coagulation and non-wetting features, and includes.

Fibrin fibre generation was observed despite the use of EDTA or sodium citrate (with anti-coagulation properties), and occurred on both the SHP CNF/PTFE and CNF/PDMS surfaces (FIGS. 4, 7 and 8), but it was not observed on hydrophobic surfaces with a low CNF concentration or no CNF (FIG. 13). FIG. 7, comprising FIGS. 7a to 7h, shows progressive fibrin fibre generation at the receding side of a 20 µl EDTA blood droplet sliding down a superhydrophobic CNF/PTFE Ti surface. A similar fibrin fibre generation phenomenon was observed for EDTA or citrated blood/PPP droplets sliding on the CNF/PTFE surface. FIG. 8 shows citrated blood generated fibrin fibres 800 on the superhydrophobic CNF/PTFE and CNF/PDMS surfaces 802. FIG. 8a shows a 20 µl water droplet 804 sitting on the superhydrophobic CNF/PTFE Ti mesh 806. FIG. 8b shows fibrin fibres 800 generating at the receding side of a 40 µl citrated blood droplet 808 on the superhydrophobic CNF Ti mesh. FIG. 8c shows a 20 µl water droplet 804 sitting on the superhydrophobic CNF/PDMS Ti surface 810, and FIG. 8d shows fibrin fibres 812 generating at the receding side of a 20 µl citrated blood droplet 814 on the superhydrophobic CNF/PDMS Ti surface 816. Fibrin fibres were also observed for PPP with EDTA on this CNF/PDMS Ti surface.

Figure 9:
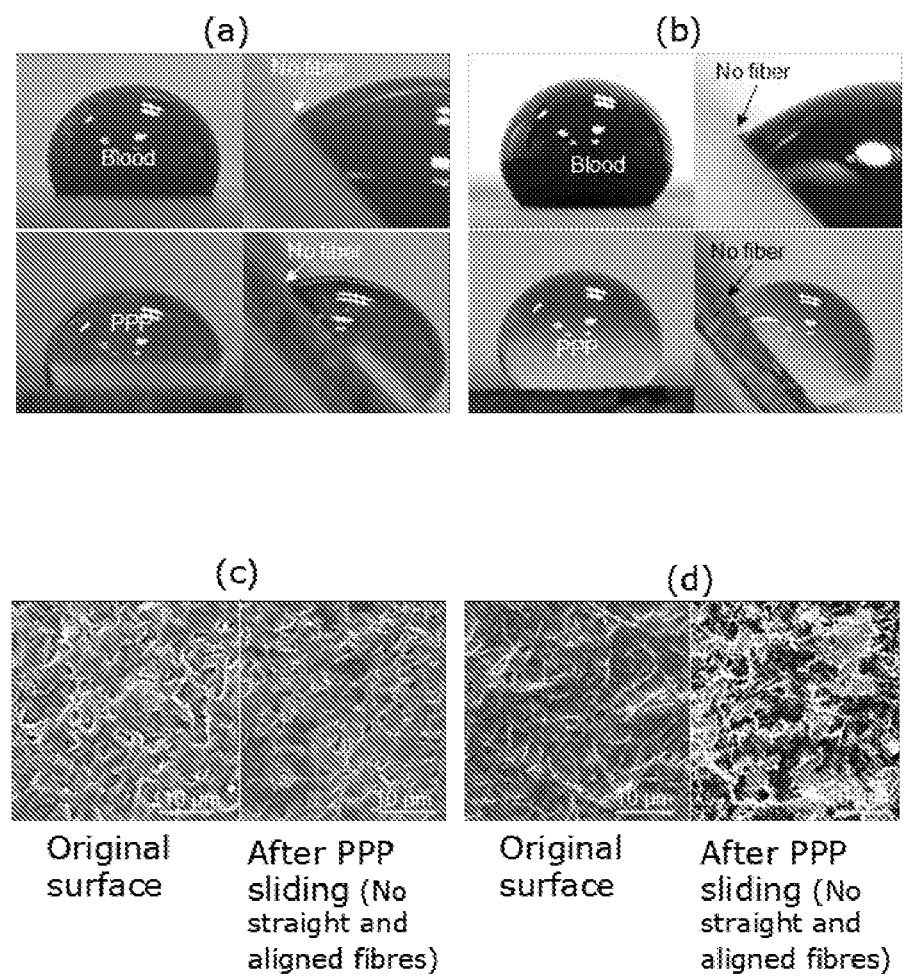
FIG. 9 shows an absence of fibrin fibres generating on the hydrophobic CNF surfaces, and particularly.

A similar fibrin fibre generation phenomenon was observed for all EDTA or citrated blood/PPP droplets sliding on the CNF/PTFE Ti mesh and the CNF/PDMS Ti surfaces. FIG. 9 shows that no fibrin fibres were generated on the hydrophobic CNF surfaces. FIG. 9a shows no fibre observed for 20 µl EDTA blood or PPP droplets on the HP #1 sample, spray-coated with only PTFE. FIG. 9b shows that no fibre was observed for 20 µl blood or PPP droplets on the HP #2 sample, spray-coated with 0.2 wt % CNF in PTFE. FIG. 9c provides SEM images of the HP #1 surface before and after PPP sliding, showing no straight fibrin fibres on the surface. Instead, the surface became bio-fouled by plasma. Similar results were observed on this surface after blood sliding. FIG. 9d provides SEM images of the HP #2 surface before and after PPP sliding, showing no straight fibrin fibres on the surface. The surface also became bio-fouled by plasma. Similar results were observed on this surface after blood sliding.

This suggested that the nano-engineered SHP CNF surface promoted fibre formation and the choice of PTFE or PDMS for CNF immobilization would not affect the fibre generation.

Figure 10:
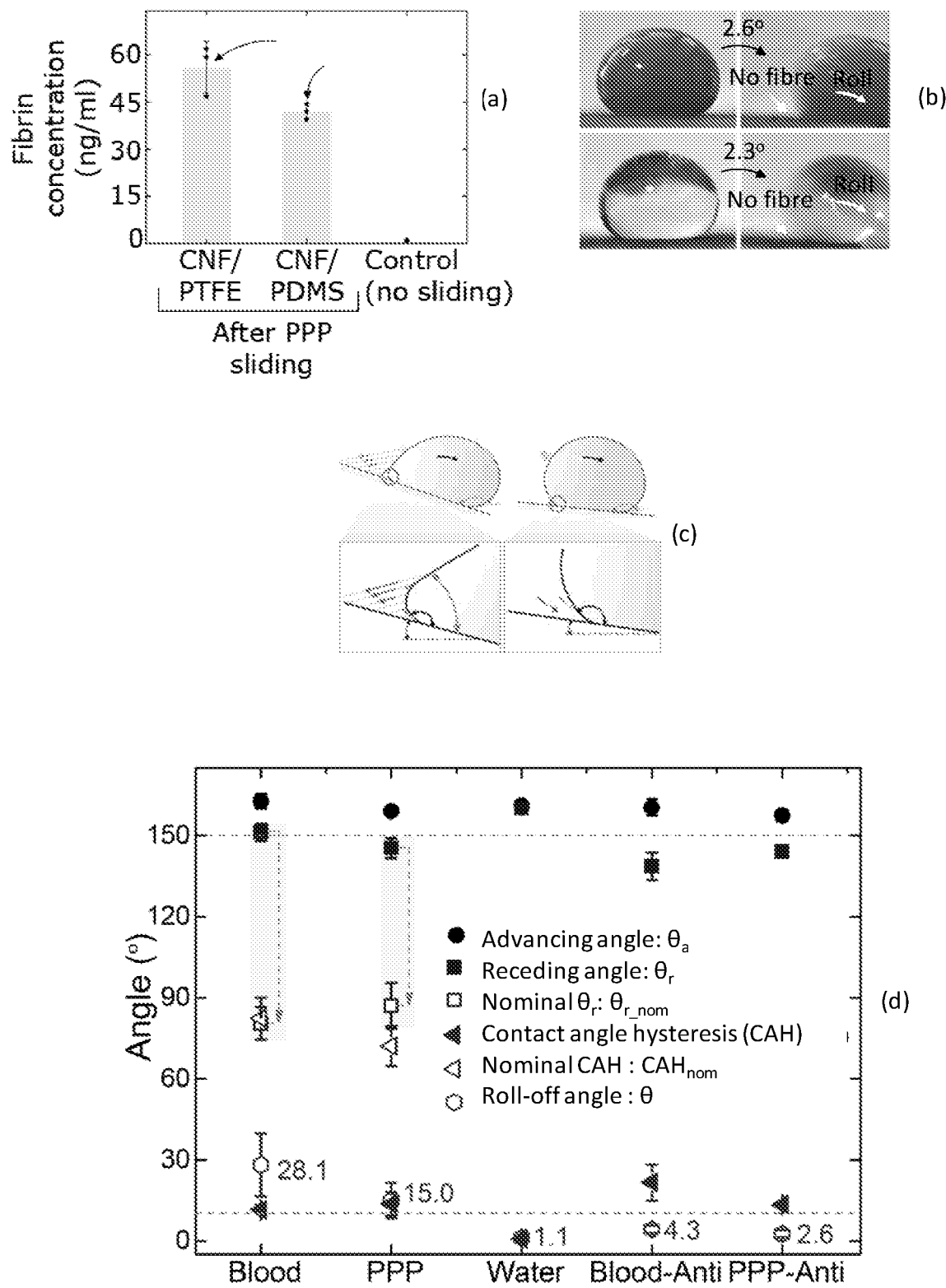

Fibrin presence was then confirmed. To confirm that these fibres were indeed fibrin, verification tests were performed. Existence of fibrin, on both the SHP CNF/PTFE and CNF/PDMS surfaces after PPP sliding, was verified through porcine fibrin enzyme-linked immunosorbent assay (ELISA) tests. A standard dilute solution from the ELISA kit was flushed over the CNF surface with and without PPP sliding to wash the generated fibrin fibres into the reaction well for a qualitative analysis. The positive results in FIG. 10a confirmed the fibres to be fibrin (data in FIGS. 10a and 10d are shown as mean±standard deviation (SD), the error bar represents SD, and individual data points in FIG. 10a are represented by black stars).

To further support this result, it was found that adding anti-thrombin to the blood/plasma could prevent fibre formation (see FIG. 11a). As thrombin is a key factor for fibrin formation, thrombin inhibition is a potent way to prevent fibrin generation. A high dose (2 mg ml$^{-1}$) of a thrombin inhibitor, argatroban, was used in EDTA or citrated blood and PPP, and it was found that both blood and PPP droplets (20 µl) quickly rolled off the SHP CNF surface at a very small angle without generating any fibres (FIG. 10b). SEM imaging further confirmed the absence of aligned long fibrin fibres on the surface after sliding by anti-thrombin containing blood or plasma (FIGS. 11b and 11c). Similarly, fibrin formation was not detected in the touch-lift test with such anti-thrombin treatment (FIGS. 11d to 11f). These findings collaboratively confirmed the identity of the fibres as fibrin.

Figure 11:
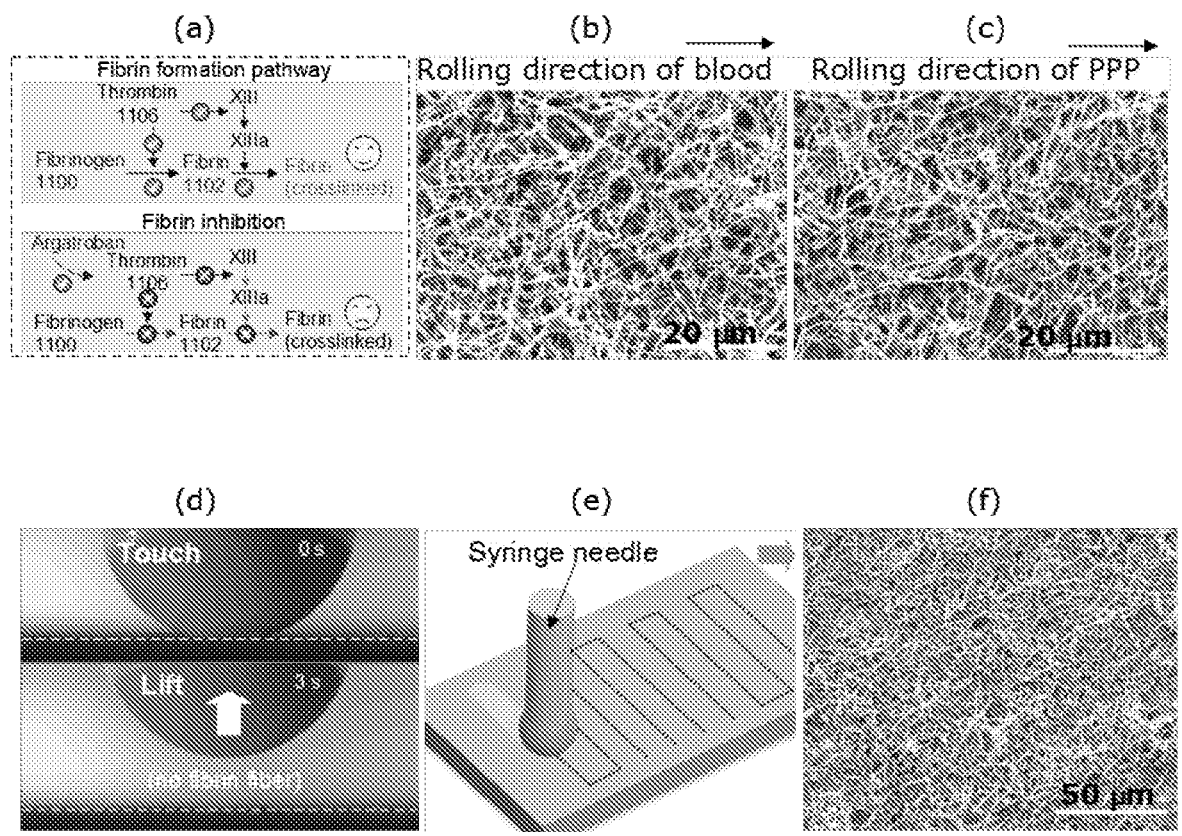
FIG. 11 shows that no fibrin fibre was generated on the superhydrophobic CNF/PTFE Ti surface, for blood/PPP with anti-thrombin, and particularly.

With reference to the particular images in FIG. 11, no fibrin fibre was observed as generating on the superhydrophobic CNF/PTFE Ti surface, for blood/PPP with anti-thrombin. FIG. 11a shows fibrin inhibition by anti-thrombin, argatroban. FIGS. 11b and 11c are SEM images of the CNF surface after sliding by anti-thrombin blood and PPP, respectively, showing no aligned/straight fibrin fibre. FIG. 11d shows that no fibrin fibre was detected when a blood drop with anti-thrombin came into contact and was subsequently lifted from the superhydrophobic CNF surface. FIG. 11e shows swiping the CNF surface by PPP with anti-thrombin generated no fibrin fibres. FIG. 11f is a SEM image of the CNF surface after PPP swiping test, showing no aligned/straight fibrin fibre.

Fibrin fibres generated at the receding side (FIG. 4d) greatly affected the sliding dynamics of blood/plasma droplets on the present SHP CNF surfaces. First, fibrin fibres behaved similar to micro-strings pulling on the blood/plasma droplets, retarding the rolling-off motion and increasing the adhesion of blood/plasma droplets on the surface (FIG. 10c, in which $\theta_a$ is the advancing angle, $\theta_r$ is the actual receding angle, and $\theta_{r\_nom}$ is the nominal receding angle.

Figure 12:
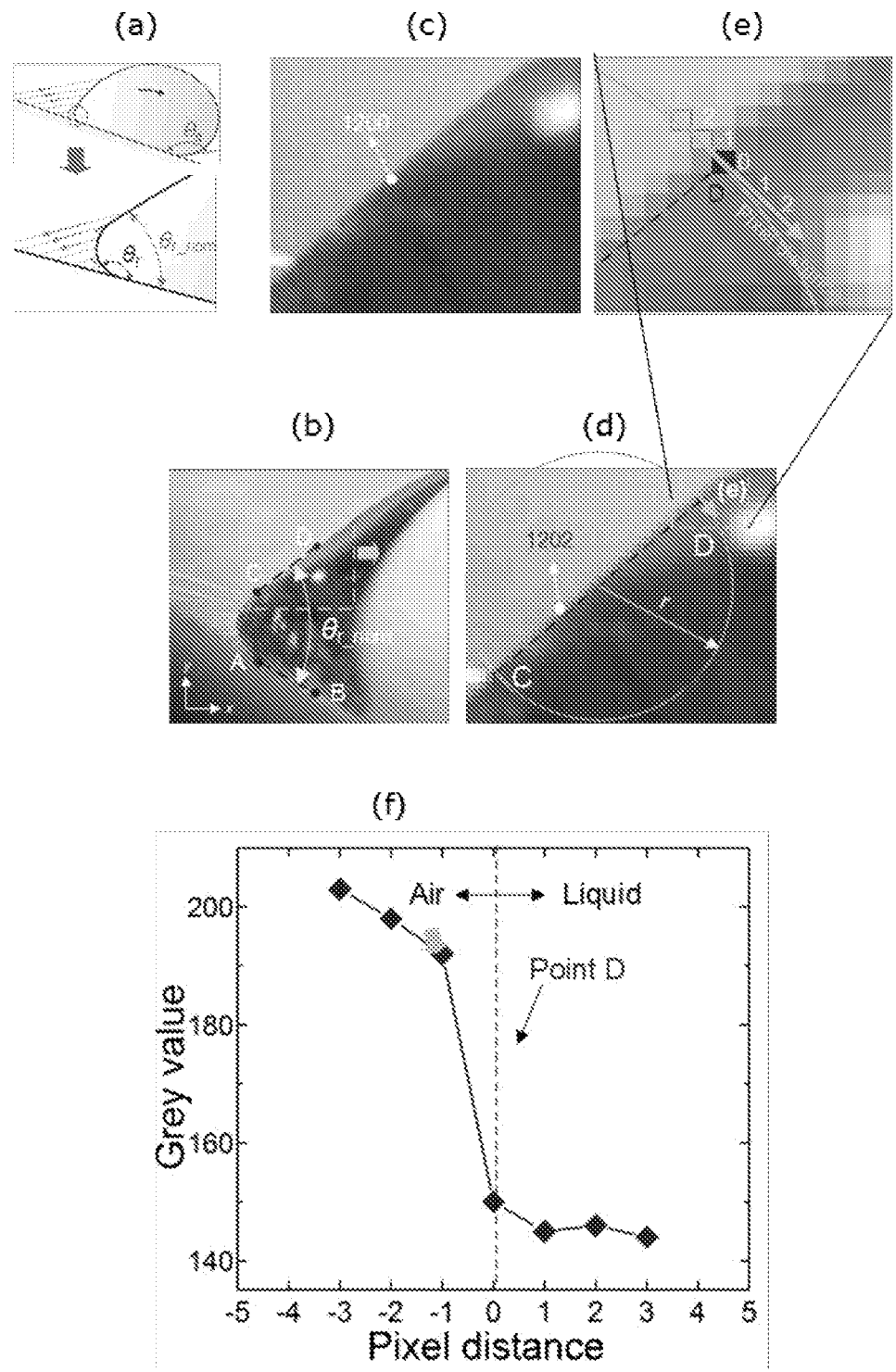
FIG. 12 shows angle measurements during testing, schematically and photographically, and the related results. In particular.

Measurement of $\theta_{r\_nom}$ is explained with references to the images in FIG. 12, showing the nominal receding angle. In FIG. 12a, the nominal receding angle $\theta_{r\_nom}$ is different from the actual receding angle $\theta_r$ for blood or PPP droplets on the superhydrophobic CNF surfaces, due to the droplet protrusion. In FIG. 12b, $\theta_{r\_nom}$, measured at the moment before catastrophic fibrin fibre fracture and droplet rolling down, is shown as the angle between line AB and line CD. AB is at the droplet-substrate interface and CD is at the straight portion of the droplet-air interface above the droplet protrusion. FIG. 12c shows the liquid-air interface 1200, that is blurry on the high-resolution (1920×1080 pixels) black and white image. FIG. 12d shows the liquid-air or liquid-substrate interface smoothed via pixel intensity averaging and reducing pixel resolution image to 480×270 pixels. This smoothened image made it easier to localize lines AB and CD. A reference circle, with a radius r of 30 pixels, was drawn to intersect the straight portion of the liquid-air interface at two points C and D. FIGS. 12e and 12f show the position of D being further confirmed at the point on the circle where the pixel grey value had an abrupt change. The position of C was confirmed similarly. Line AB on the liquid-solid interface 1202 was determined using the same method in FIGS. 12d to 12f. These procedures were performed manually and had sufficient accuracy, with errors being in the order of a pixel width, which translated to an angle error of about 0.95° (equal to arctan(1/60)).

The roll-off angle (RA) for blood and PPP droplets (mean±SD) were 28.1±11.6° and 15.0±6.6°, respectively—FIG. 10d, showing the dynamic contact angles for water droplets and blood or PPP droplets with and without anti-thrombin on the superhydrophobic CNF/PTFE Ti surface (n=4), contact-angle hysteresis $CAH=\theta_a-\theta_r$, and nominal contact-angle hysteresis $CAH_{nom}=\theta_a-\theta_{r\_nom}$. The droplet volume is 20 µl, Blood-Anti or PPP-Anti, respectively, represents blood or PPP with anti-thrombin. When fibrin generation was inhibited by anti-thrombin, blood and PPP droplets could roll off at a smaller RA of 4.3±1.4° and 2.6±1.3°, respectively. Due to the dose effect of anti-thrombin, some micro-fibrin fibres may still exist at the liquid-solid interface, affecting the receding CA and leading to a large CAH (CAH>RA) for blood/PPP droplets with anti-thrombin (see FIG. 10d). Second, the blood or plasma droplet formed a protrusion at its receding region near the surface under the tugging force from fibrin fibres (see FIG. 4d) as shown in progressive images FIGS. 7g to 7h, generating a nominal receding angle $\theta_{r\_nom}$ that was smaller than the actual receding angle $\theta_r$ (FIG. 10c). Consequently, the droplet demonstrated a large nominal CA hysteresis $CAH_{nom}$ ($CAH_{nom}=\theta_a-\theta_{r\_nom}$, actual $CAH=\theta_a-\theta_r$ and $\theta_a$ is advancing in angle). This is not customarily observed on SHP surfaces, which typically have low RAs corresponding to low contact-angle hysteresis.

Regarding the generation mechanism, fibrin fibres were initiated upon the blood/plasma contact with CNFs. Exposure to CNFs would trigger an extrinsic coagulation cascade reaction, causing the formation of thrombin from prothrombin, and subsequently converting fibrinogen into fibrin monomer. Fibrin monomers would attach onto CNF and then self-polymerize into long insoluble fibrin fibres, which became visible upon blood/plasma-substrate separation (see FIGS. 4b and 4c). An interesting and unexpected observation in this study is that fibrin fibres still generated despite the presence of anticoagulant EDTA or 3.8% sodium citrate (see FIGS. 4b, 7 and 8), demonstrating its potency in expediting fibrin formation. In addition, CNFs were reported to activate platelets, bind serum albumin and fibrinogen, and activate the serum complement system, which would further trigger coagulation. Also, electric charges concentrated on sharp geometries, such as on the tips of long CNFs, could attract fibrinogen adsorption and possibly promote coagulation.

The capability of CNFs to promote fibrin fibre formation was further demonstrated by cultivating EDTA PPP on the present CNF surface at 37° C. for 4 minutes, following published methods. A fibrous fibrin meshwork was observed to form (see FIG. 13a). Such a fibrous meshwork could be beneficial for hosting activated platelets and blood cells to accelerate coagulation, making the present superhydrophobic CNF surface promising for haemostatic applications.

An important aspect of many medical devices, and particularly wound dressings and the like, as that they are have anti-bacterial properties or can have those properties imparted to them prior to use. The present SHP CNF surfaces demonstrated excellent anti-bacterial properties. A solution containing *Escherichia coli* (a major infection-causing bacteria) was flushed with green fluorescence protein (GFP) expression plasmid over a glass slide that was half-coated with CNFs and nearly no bacteria was found on the SHP CNF surface under the confocal microscope with a 473 nm laser for GFP excitation. FIG. 13b shows that after flushing with fluorescent bacteria solution, nearly no bacteria (dots) were observed to attach on the superhydrophobic CNF surface under the microscope with green fluorescent protein excitation.

The low adhesion of bacteria on the present SHP CNF surface is attributed to the low surface energy hydrophobic materials and the micro/nano-roughness. This excellent anti-bacterial capability will be beneficial, as it helps keep the haemostatic patch sterile and prevent wound infections.

Figure 14:
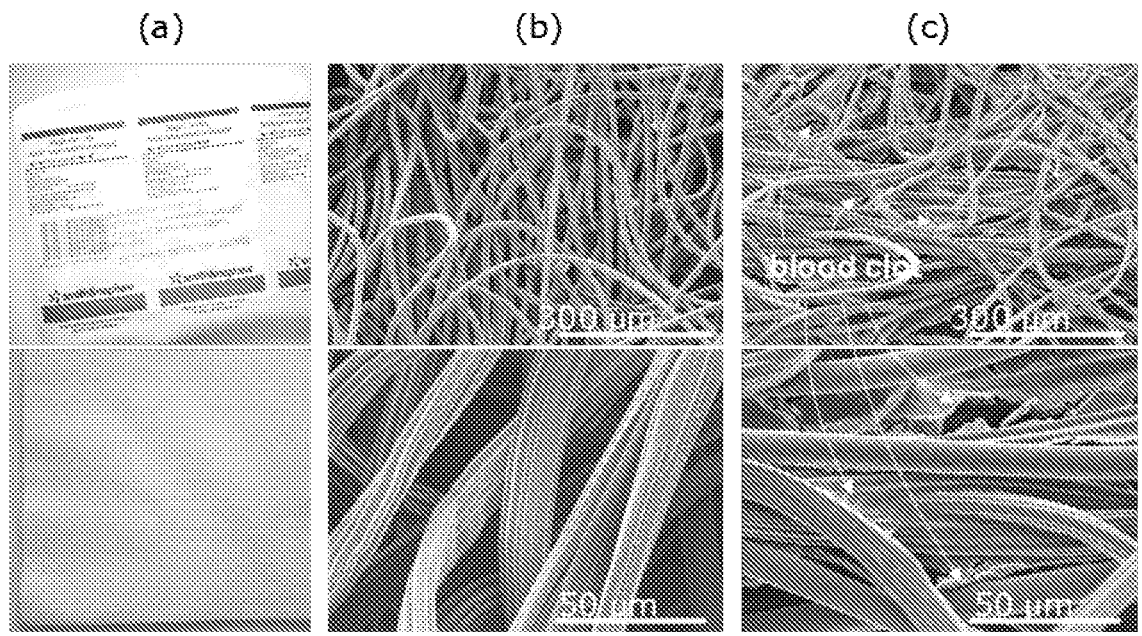
FIG. 14 shows a normal cotton gauze and, in particular.

In addition to being anti-bacterial, a haemostatic material should promote quick coagulation to minimize blood loss. As a proof-of-concept prototype of using the present material as a wound patch, a normal cotton gauze was coated with SHP CNF as shown in FIG. 13c. The normal gauze is superhydrophilic and blood absorbing. The CNF gauze has a dense layer of CNF coating and repels blood. As cotton could not withstand the high annealing temperature (400° C.) for CNF/PTFE coating, CNF/PDMS was used for coating, taking advantage of the low polymerization temperature of PDMS. As verified previously, the CNF/PDMS surface can promote fibrin fibre generation just like the CNF/PTFE surface (see FIG. 8d). The cotton gauze, which was initially superhydrophilic and blood absorbing (see FIG. 14), became SHP after the CNF/PDMS coating (FIG. 13c). FIG. 14 shows normal cotton gauze with FIG. 14a providing optical images of the uncoated gauze, FIG. 14b being SEM images of the uncoated gauze, and FIG. 14c being SEM images of the gauze with clot, the clot and gauze being a solid piece.

Figure 15:
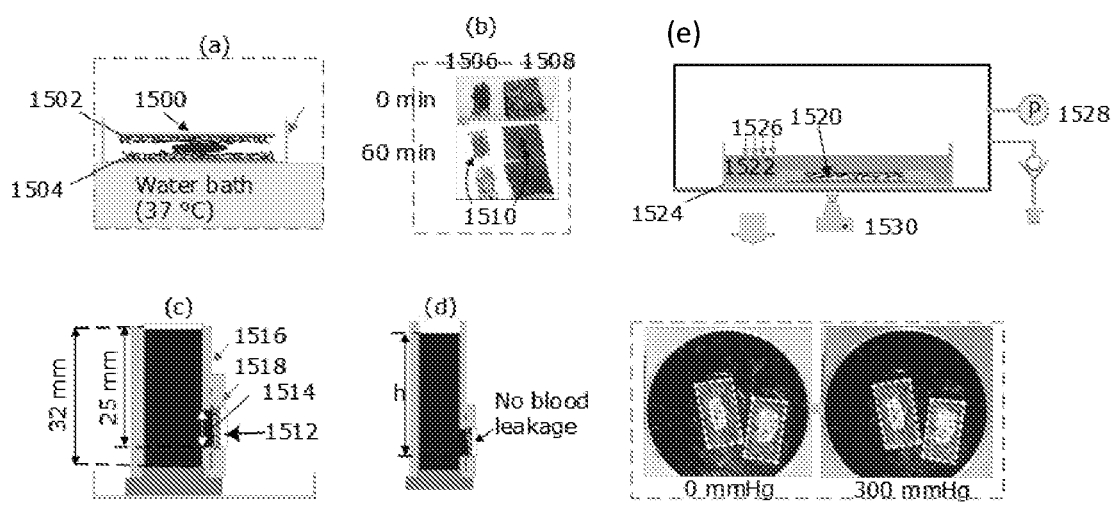
FIG. 15 illustrates in vitro clotting tests. In particular.

The clotting performance of this superhydrophobic CNF gauze was then evaluated. Evaluation via In vitro clotting tests is shown in FIG. 15. FIG. 15a shows a schematic of a clotting test by sandwiching 20 µl blood between 1500 two gauze samples 1502, 1504 (size: 15 mm by 15 mm). For the superhydrophobic CNF gauze, blood was contacting the surface coated with CNF. FIG. 15b shows the nominal blood contact area 1510 of 20 µl blood on the uncoated white cotton gauze 1506 (FIG. 14a) and a superhydrophobic CNF-coated gauze 1508. The blood became sufficiently coagulated after 60 minutes, making it easier to separate the two gauzes and to measure the blood contact area. The blood contact contour is highlighted by the white line. FIG. 15c shows clotting without blood loss. The superhydrophobic CNF gauze 1512 was used to seal an opening 1514 (8 mm by 5 mm) on the silicone tube 1516 by medical tape 1518, which was subsequently filled with blood, initiating coagulation by adding $CaCl_2$). FIG. 15d provides the measurement of the maximum hydrostatic pressure that one layer of the CNF gauze (without an impervious membrane) can withstand before blood leakage. The maximum blood column height h without blood leakage was used to calculate the blood leakage-free pressure. FIG. 15e shows non-wetting of the CNF gauze 1520 by blood 1522 under a high pressure of 33 mmHg. The CNF gauze, the periphery of which (not the central region) was glued onto the petri dish 1524, was immersed in the citrated blood, in a pressure chamber with the CNF surface contacting blood. The petri dish acted as an impervious membrane to retain the air plastron across the CNF/blood interface. The hydrostatic pressure exerted onto the CNF surface in blood was controlled by pumping air into the pressure chamber and monitoring the air pressure 1526 using a pressure sensor 1528. A camera 1530 projecting upward was used to detect whether the central part of the CNF gauze was wetted by blood at a given pressure. In comparison, it was experimentally observed that the normal gauze instantly got wetted by blood at ambient pressure. The CNF coating was in contact with blood in these tests.

Figure 20:
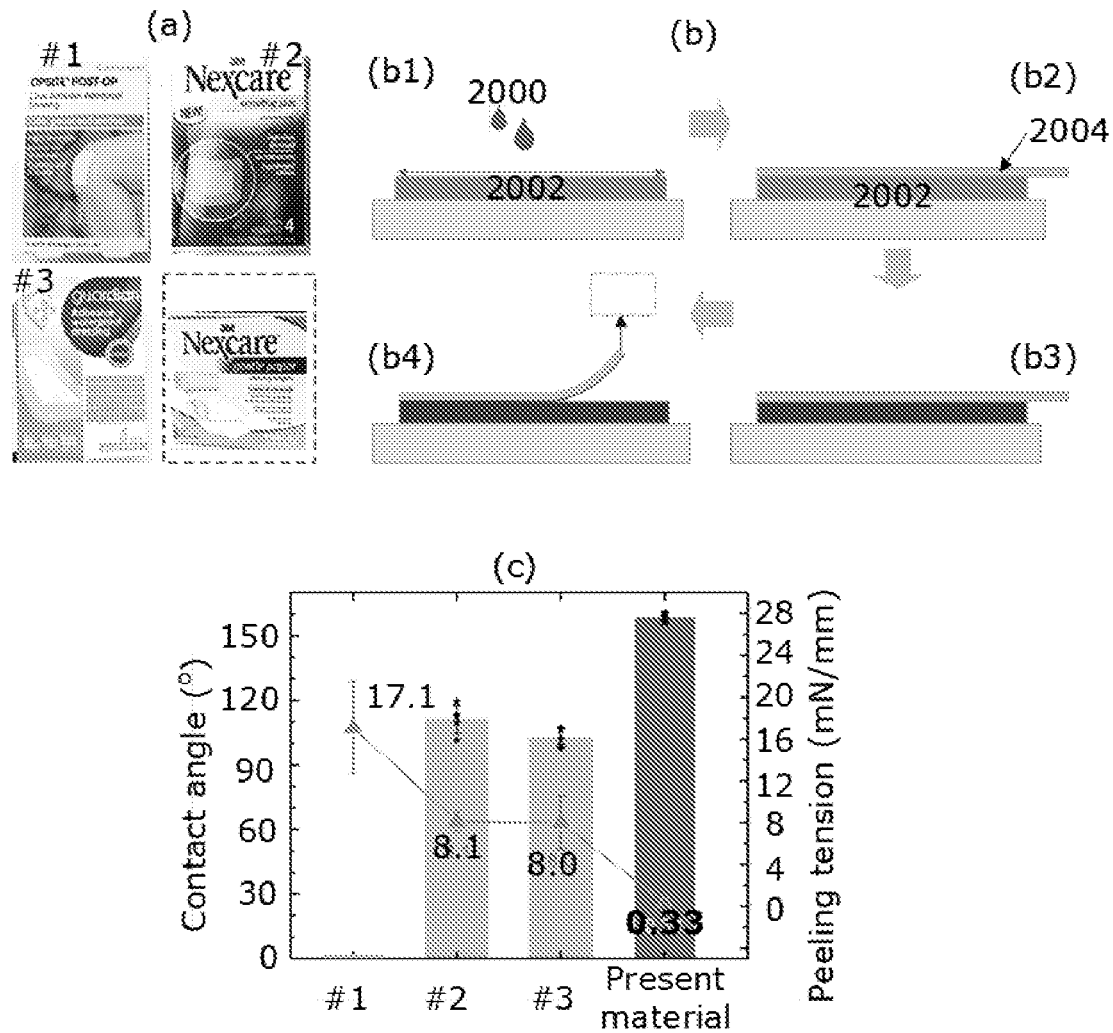

With reference to FIG. 15a, 20 µl blood 1508, placed between two pieces of gauze 1510, 1512, was allowed to coagulate for a fixed time. Coagulation was terminated by adding 10 ml deionized (DI) water. Free haemoglobin from red blood cells, not trapped in the clot, was released into water and was assayed. A lower haemoglobin level indicates faster clotting. The CNF gauze was shown to have a lower haemoglobin level and thus faster clotting compared to normal gauze, at 3 minutes. FIG. 13d shows the relative haemoglobin absorbance RHA(t) plot, demonstrating the fast clotting performance of the CNF gauze. As the experiment was performed in a petri dish 1514, clotting in the petri dish 1514 without any gauze was used as control. The absolute haemoglobin absorbance at clotting time t, HA(t), was measured by the spectrometer at 540 nm (n=3), HA(0). The haemoglobin absorbance at t=0 min was used as the reference, and the relative haemoglobin absorbance at clotting time t, RHA(t), equals HA(t)/HA(0). As the haemoglobin came from unclotted red blood cells, a lower haemoglobin absorbance value would mean faster clotting.

The non-wetting property of the present SHP CNF coating can prevent blood loss at the wound site, by keeping blood within the wound. This feature was demonstrated in vitro, with a silicone tube filled with blood that had a hole opened on its side to mimic a bleeding wound. Cotton gauzes, with and without SHP CNF coating, were used to cover the holes (see FIG. 15c). The SHP CNF gauze achieved clotting without blood loss, whereas the normal cotton gauze experienced severe blood seepage. See FIG. 13e, clotting without blood loss over three measurements using the CNF gauze 1300 to seal an opening 1302 on a silicone tube 1304, mimicking a skin wound covered by a gauze. Individual data points are represented by black indicia. The CNF coating was in contact with blood in FIG. 13d and FIG. 13e. The scale bars are 10 µm in FIG. 13a, 50 µm in FIG. 13b, and 20 µm in FIG. 13c. Data in FIG. 13d and FIG. 13e are shown as mean±SD, and the error bar represents SD. Therefore, owing to the CNF coating's synergetic capability of promoting fibrin formation and minimal wetting (superhydrophobicity), the present material design strategy can achieve fast clotting without blood loss. This performance can be especially beneficial for chronic bleeding disorders.

Furthermore, the air plastron trapped on the SHP CNF surface can be a functional component of the SHP wound patch, as it can help retain the non-wetting feature under high pressure. Without an impervious plastic membrane (see FIG. 13e), a single layer of CNF gauze could withstand a pressure of 4.9±0.3 mmHg (mean±SD) without blood infiltration (see FIG. 15d); with a impervious plastic membrane applied at the back of the gauze like the plaster, the trapped air plastron could prevent the CNF gauze immersed in blood from wetting even at 300 mmHg (FIG. 15e), which was significantly larger than a lotus leaf's non-wetting pressure (about 100 mmHg).

Another unexpected and rather inherent feature of the SHP CNF patch is that the formed clot can easily detach from the CNF gauze by itself upon clot maturation. This is in sharp contrast to existing hydrophilic haemostatic dressing materials—blood will soak and coagulate inside the pores of these materials and the generated clot-dressing composite mixture has strong adhesion to the wound and can be difficult to detach (see FIG. 14c). Forced peeling of these hydrophilic haemostatic dressings will tear the wound and cause secondary bleeding, complicating subsequent wound care.

Figure 17:
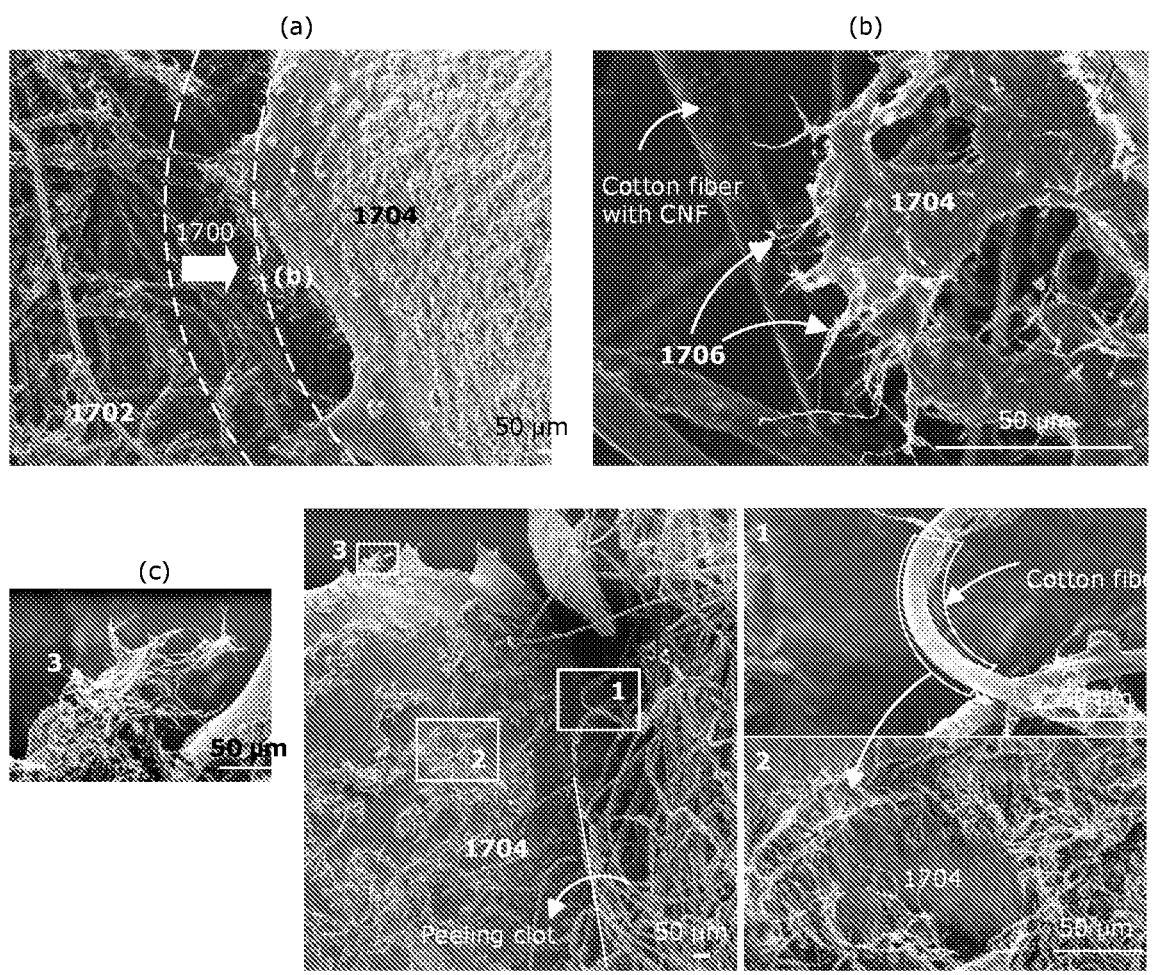

It was presently found that the driving force for easy clot detachment from the present CNF gauze was the contraction of clot as it matured. In the early stage of coagulation, fibrin fibres would form a fibrin meshwork for clot formation. This fibrin generation was initiated on CNFs as illustrated in FIG. 6a in which fibrin fibres 1600 form from blood 1606 on a superhydrophobic CNF surface 104. Due to its non-wetting property and the presence of micro-air pockets, the CNF surface would only partially attach onto the clot. As such, the clot would have micro-fibrin fibres connected onto the CNFs as shown in FIG. 16c and FIG. 17. Therefore, a weak connection between the clot 1704 and the CNF surface 1702 was formed due to the presence of air pockets 1600 at the blood-substrate interface—this is call a "Cassie-Baxter" state. During clot maturation, filopodia from platelets would pull and bend fibrin fibres 1706, generating a contractile stress and causing clot contraction 1602—see FIGS. 18d and 17a (reference 1700 for CNF gauze 1702). FIG. 17d shows clot contraction on the CNF Ti mesh. The clot border contracted inwards from the initial blood-substrate contact line. The contractile stress in the clot would pull and remove micro-fibrin fibres adhered on CNFs 604. As shown in FIG. 16b, during clot maturation the fibrin mesh would squeeze out the serum and shrink the clot into a smaller size. Contractile stress during clot contraction and solidification would remove CNFs connected with micro-fibrin fibres, causing the clot to free itself from the superhydrophobic CNF surface after clot solidification and contraction.

Self-peeling behaviour of the clot was observed on the rigid Ti mesh substrate coated with CNF after clot contraction as shown in FIG. 16e, along contraction directions X, X', and self-peel direction Y, and in FIGS. 18d to 18f, in which FIG. 18d shows the initial clot position 1800, and final clot position 1802 after contraction in direction 1804, FIG. 18e shows a clot self-detached from the CNF Ti mesh, showing localized contact between blood and the Ti mesh, and in which FIG. 18f shows the hairy area on the clot which was in contact with CNF. On the flexible CNF gauze, clot peeling was not visibly self-accomplished, as cotton fibres would be deformed by clot contraction. However, the clot could be easily picked off (see FIG. 16f). The average clot-peeling tension for the present SHP CNF gauze was about 1.7±1.5 mN mm$^{-1}$ (mean±SD). This is about 54 times smaller than that for the normal hydrophilic gauze, which was about 91.3±19.4 mN mm$^{-1}$ as shown in FIG. 16f over four measurements.

After clot detachment, CNFs that were initially immobilized on cotton fibres were transferred onto the clot, making the cotton fibres appear smooth—which was drastically different from their original appearance in FIG. 5c—and the detached clot surface appear hairy—see also FIG. 16d. FIG. 17c includes a close-up view of FIG. 16d and provides SEM images of the clot surface in contact with the CNF gauze after clot detachment, with localized contact between blood and the CNF gauze. 1700 and 1702 show CNFs transferred onto the clot after clot detachment, resulting in a smooth cotton fibre, and a hairy clot surface. 1704 shows micro fibrin fibres initially attached onto CNFs. This intrinsic clot self-detachment mechanism thus greatly facilitates wound dressing removal, avoiding wound tear and eliminating secondary bleeding.

The clot-peeling force of the present material was also compared with three representative commercial haemostatic products shown in FIG. 20a. The Nexcare hydrophilic dressing material from 3 M was used as the substrate material for clotting to occur (FIG. 23b). The Nexcare substrate material (25 mm wide and 100 mm long) was adhered onto the stainless base. Citrated blood mixed with 0.2 M $CaCl_2$) solution at a volume ratio of 10:1 (2000) was then dispensed onto the substrate 2002 to soak it with blood (b1). Haemostatic samples 2004 (30 mm long and 10 mm wide) were immediately placed onto the substrate material 2002, allowing the clot to form between the haemostatic sample 2004 and the substrate material 2002 (b2). Clotting was first allowed to occur at 37° C. for 1 h. Clot solidification was subsequently accelerated by exposing the clotted samples to warm air flow from a hair dryer for 30 min (b3). After that, samples were peeled from one side to measure the peeling force (b4)—see also FIG. 23b. Peeling tension was calculated as the maximum peeling force divided by the sample width (repeated for three times; n=3). Besides, WCA was measured with 10 μl DI water (n=5) to provide information on hydrophobicity for different samples (FIG. 23c). These three commercial products are marketed as low-adherence or pain-free on removal, but the clot-peeling tension of the present material is 24-52 times smaller that the clot-peeling tension of the commercial haemostatic products, as shown in FIG. 20c. Specifically, the clot-peeling tension on the present material is about 52 times smaller than that of one of the representative commercial haemostatic products and about 24 times smaller than that of the other two representative commercial haemostatic products. Therefore, the present material design strategy has brought the clotting peeling force of haemostatic materials to a very low level.

Figure 19:
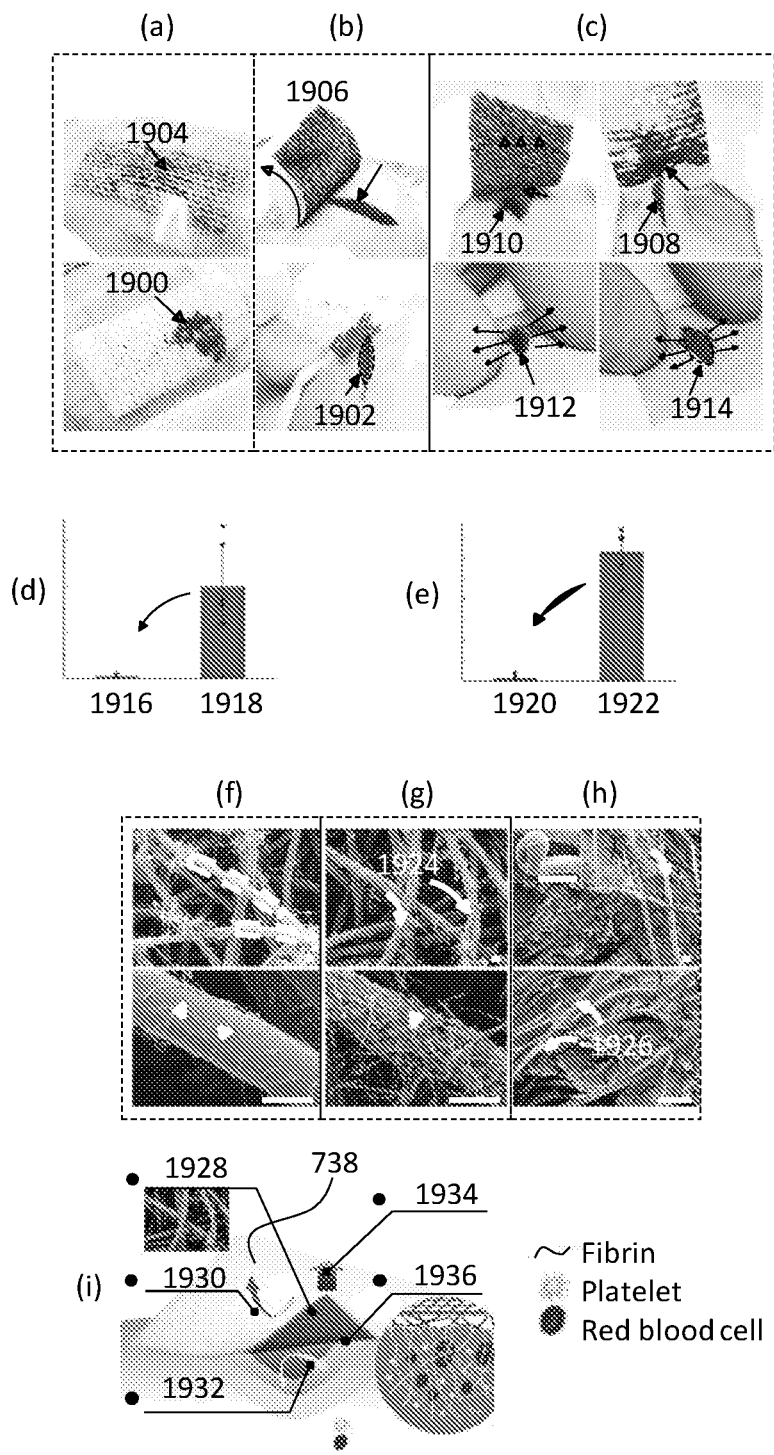
Figure 21:
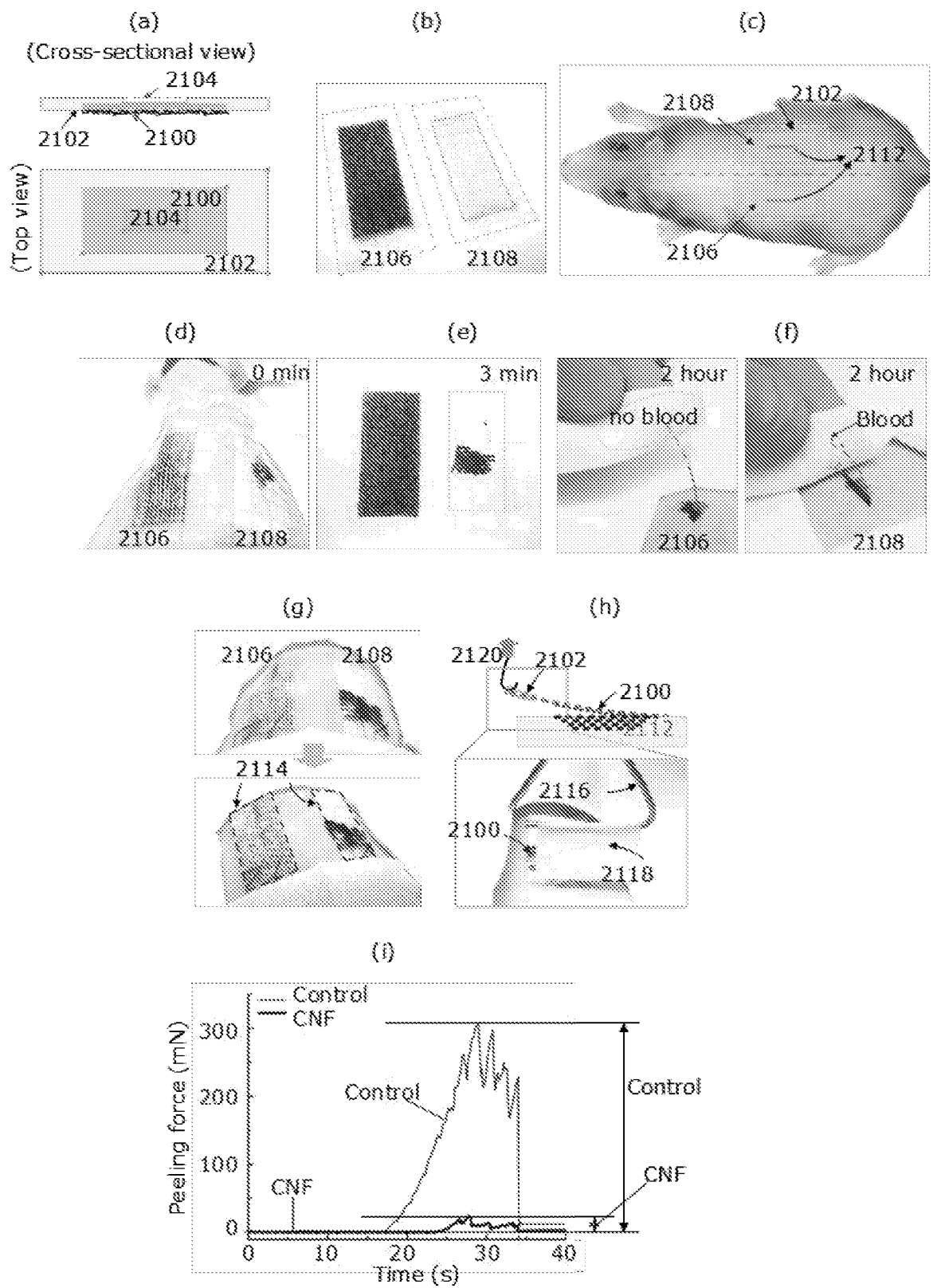

To verify the aforementioned features of the present haemostatic material, in vivo experiments were performed on rats with the back-bleeding model—incisions made on the back of rats for gauze application—as shown in FIGS. 21c and 21d. The normal gauze was blood absorbing, leaving behind an open wound as referenced by numerals 1900, 1902 in FIGS. 19a and 19b. For FIG. 19a, the plaster-like gauzes were patched onto incisions on the back of a rat—the control cotton gauze got wet quickly, while the CNF gauze prevented blood loss. For FIG. 19b the gauze was peeled at 3 min to measure the blood loss. The CNF gauze helped form a gel-like clot, which properly sealed the wound. Under the control gauze, an open wound was observed. In contrast, no blood was observed to seep through the CNF gauze 1904, as shown in FIG. 19a. This demonstrates the excellent blood-repelling property of the present devices.

In addition, a darkened gel-like clot was observed under the CNF gauze 706 at 3 min as shown in FIG. 19b. This clot properly sealed the wound whereas the wound remained open under the control gauze, demonstrating the ability of the CNF gauze to promote coagulation in vivo. The average blood loss for the CNF gauze was 0.3±0.7 mg as shown in FIG. 19d (reference 1916), which was about 1.5% of that for the normal gauze at 19.8±9.0 mg as shown in FIG. 19d (reference 1918). Blood loss was characterized by the weight increase in gauze at 3 min—see photo in FIG. 21e for comparison of the CNF gauze and control gauze at 3 min. This confirms the ability of the CNF gauze to minimize blood loss. Thus, in vivo work corroborated the present in vitro findings—the blood-repelling CNF gauze could promote coagulation, minimize blood loss, and help achieve a good clot-sealed wound.

The force required for gauze removal was also measured in vivo. As the wound under the normal gauze 1908 was torn seriously during peeling, it was difficult to accurately measure the gauze-wound contact width. See FIG. 19c, showing peeling of the gauze at 3 min to measure the blood loss. The CNF gauze helped form a gel-like clot, which properly sealed the wound. By comparison, under the control gauze, an open wound was observed. The maximum peeling force was used to qualitatively evaluate the performance of the present CNF gauze (FIG. 22i). The average maximum peeling force (mean±SD) for the CNF gauze was 7.2±8.6 mN as indicated by reference 1920 in FIG. 19e. This measurement was about 43 times smaller than that for the normal gauze, at 315.2±61.3 mN—see FIG. 19e, reference 1922. As shown in FIG. 19c, reference 1910, the present, easy-to-peel CNF gauze did not tear the wound due to CNF detachment. Many CNFs that were initially coated on cotton fibres as shown in FIG. 19g (reference 1924) were removed during clot peeling just like in in vitro tests—FIG. 19h shows cotton fibres 1926 embedded in a clot. Moreover, gentle stretching did not cause wound tearing (see FIG. 19c, reference 1912) or secondary bleeding, whereas peeling the normal gauze tore the wound and caused bleeding—see FIG. 21f. In the control group, the clot strongly bound the wound and even skin hairs (see FIG. 19c, 1914) to the gauze, forming a stiff clot-gauze-hair concrete. FIG. 7h shows SEM images of the peeled normal gauze in FIG. 19c, showing a clot-gauze-hair concrete, with rat skin hairs imbedded in clot. A hair root is shown in the inset, implying that skin hairs that were stuck in the clot were pulled out from skin during gauze peeling. Forced peeling would tear the wound and cause secondary bleeding, increasing the chance of infection as shown in the top right of FIG. 19c and right-hand side of FIG. 11f. In vivo findings therefore confirm the remarkable features of the present wound-dressing materials. FIG. 19i shows nanofiber structured surface 1928, antibacterial surface properties at 1930, blood loos prevented at the wound site 1932, easy peeling in the direction of arrow 1934 without tearing the clot, and fast clotting at the wound 1936 under patch 1938. This can successfully address the serious problems—blood loss and strong clot adhesion—plaguing the application of conventional hydrophilic haemostatic materials.

Figure 24:
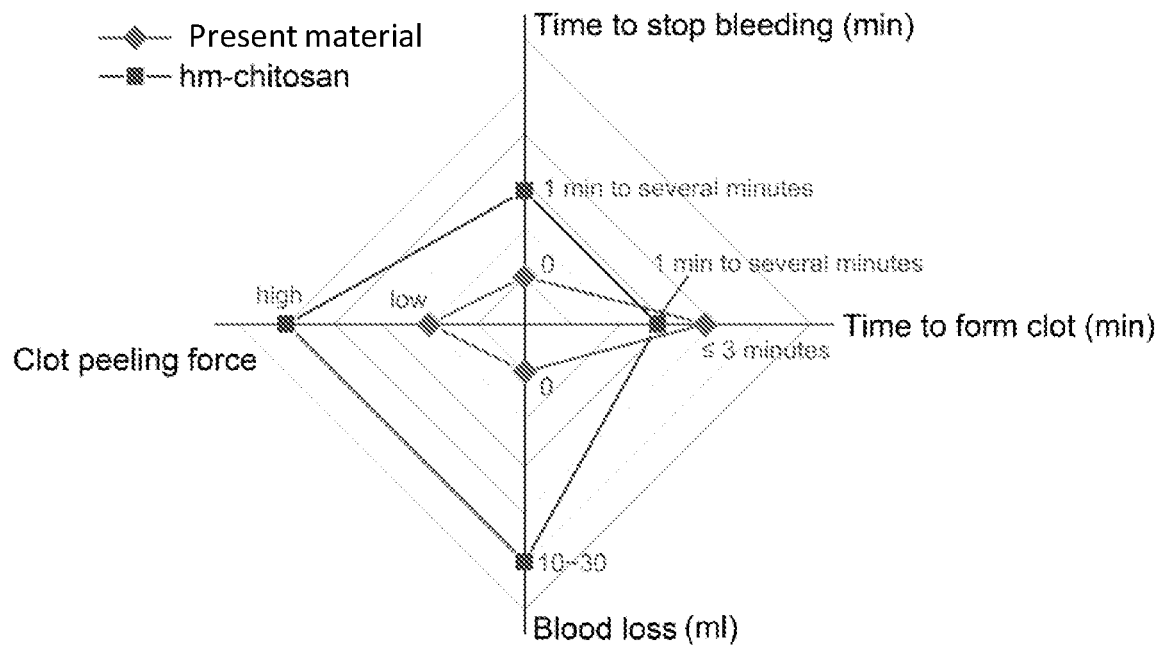
FIG. 24 shows the comparison between the present material and the hydrophobically modified chitosan from four perspectives: (1) the time to stop bleeding, (2) the time to form a clot, (3) blood loss and (4) the clot peeing force.

Studies have shown that multi-wall CNFs and the CNF/PDMS composite were non-toxic, with the 1-week cell viability exceeding 95%. The present material is designed for haemostatic purposes and will be in contact with skin for a short time. In vivo skin compatibility tests were therefore conducted by attaching a 10 mm by 10 mm patch of the present material onto a rat's skin (hair shaved) with clinically approved tape for 12 h (see FIGS. 24a and 24b). Compared with the skin under the pristine gauze (control), the skin under the present CNF gauze appeared normal and no itching or erythema was observed after 12 h (see FIG. 24c). Thus, based on previous reports on cell non-toxicity and this skin compatibility test, the present CNF/PDMS material would be safe for haemostatic use.

As described above, a strategy for the design of wound-dressing materials featuring both rapid coagulation and facile clot removal has been developed and demonstrated, based on superhydrophobicity imparted by surface-immobilized CNFs. The developed SHP haemostatic CNF gauzes are shown to simultaneously combine a host of therapeutic functionalities. First: they achieve fast clotting by expediting the formation of micro-fibrin fibres. Second: clotting without blood loss can be achieved, owing to the pressure-resistant non-wetting properties of the SHP surface. Third: there is minimal contact between the clot and the present SHP CNF surface. Driven by the contractile stress in the clot contraction phase, the SHP CNF haemostatic surface will inherently tend to detach from the clot upon clot maturation, thus allowing a natural and unforced removal of the haemostatic dressing without causing secondary bleeding.

Fourth: the SHP CNF patch can significantly reduce bacterial attachment, reducing infection risk. Finally: the CNFs are immobilized in a polymeric matrix on the gauze substrate, preventing free micro/nanoparticles or fibres from entering the vascular stream. Moreover, skin compatibility tests show that the present materials can be safe for haemostatic use.

Different from existing haemostatic products/materials, the present material works in a distinctive manner. It stops bleeding first, reinforces clotting subsequently, and enables unforced natural detachment in the end. This offers the following advantages. First: the SHP feature helps stop bleeding immediately upon application. Bleeding therefore ceases before the formation of a strong clot. This can be life-saving for haemorrhage cases such as in severe accidents and military combat, as it takes time for clotting to occur even with the most effective haemostatic materials. Second: rapid clotting is achieved by the nano-engineered surface structure, without the help of active clotting agents/chemicals. The present nano-engineered fibrous structure promotes quick growth of fibrin network to seal the wound. Clotting agents are routinely used in haemostatic products, such as the hydrophobically modified chotisan, which may provide shorter clotting time than the present material. However, the present material brings it with a distinct strategy of hastening coagulation using a nano-structuring approach also ensuring facile removal, a critical feature to avoid secondary bleeding—a quantitative comparison between the present material and the hydrophobically modified chitosan is provided in FIG. 24). The present material yields a reduction of the clot peeing force, by a good order of magnitude. Compared with commercial haemostatic products, the clot-peeling tension of the present material is about 24-52 times smaller (FIG. 23c). This natural and facile clot detachment feature is unique to SHP haemostatic materials disclosed herein.

The present methods therefore pioneer a strategy for designing more efficient haemostatic material using surface nano-engineering. It has been demonstrated that a nano-structured surface can achieve fast clotting with unique blood loss-free, unforced detachment from the wound site, and also reduced bacteria adhesion. The multifunctional material concept presented herein shows clear potential to significantly advance the state-of-the-art of wound dressings, and medical devices, bringing benefits to common wounds, surgery, and even haemophilia. In the current study, non-biodegradable carbon nanofibres were used to design the nano-engineered surface. Biodegradable nanofibres could be developed for internal use and are intended to be encompassed by the present disclosure.

For completeness, fibrin fibre generation tests (FIGS. 4 and 6 to 11) were performed using blood and platelet poor plasma (PPP) with the presence of EDTA or sodium citrate. Fresh EDTA porcine blood was collected into sterile vacutainer tubes with K2 EDTA (3.0 ml, purple) and transported in a sealed foam container with ice. PPP was obtained by centrifuging the blood in EDTA tubes first at 1800 G for 10 min (Sorvall ST 8 Centrifuge, at room temperature-20° C.) and then at 3000 G for another 10 min. As EDTA would prevent blood coagulation by irreversibly chelating calcium ions, EDTA blood was not suitable for coagulation testing. For in vitro clotting tests (see FIGS. 13 and 16), 3.8% sodium citrate was used as the anticoagulant. Citrated porcine blood from the same vendor was collected into polypropylene tubes by mixing blood with 3.8% sodium citrate solution at a volume ratio of 9:1 and was transported following the same protocol.

CAs and RAs were measured using a custom-built device. CA was measured using the sessile method by dispensing 5 μl liquids (deionized (DI) water, blood and PPP) on flat substrates (the CNF/PTFE Ti and CNF/PDMS Ti surfaces) and 20 μl liquids on the CNF Ti mesh. Dynamic CAs, including advancing CA $\theta_a$, receding CA $\theta_r$, CA hysteresis CAH (CAH=$\theta_a$-$\theta_r$), nominal receding CA $\theta_{r\_nom}$, nominal CA hysteresis $CAH_{nom}$ ($CAH_{nom}$=$\theta_a$-$\theta_{r\_nom}$), and RA $\theta$ were measured using the tilting method, by placing a 20 μl droplet (for water, blood, and PPP with or without anti-thrombin) on the sample surface and tilting the sample till droplet roll-off. For PPP or blood on the SHP CNF surface, due to the existence of fibrin fibres, RA $\theta$ was defined as the tilt angle when fibrin fibres fractured and the droplet rolled off quickly. Static and dynamic CAs were averaged over four repetitions (n=4). Surface morphology of the prepared samples and the surfaces after blood/plasma tests were characterized by SEM (SEC, SNE-4500M) after gold coating.

The anti-thrombin, argatroban (Purity: >98%) was first dissolved in 0.9% NaCl solution and then added into EDTA blood or PPP to achieve a final dose of 2 mg ml$^{-1}$, which was higher than the value used in animal studies to ensure sufficient thrombin inhibition.

The porcine fibrin ELISA kit was ordered from MyBioSource, Inc. (Catalogue #MBS261977). Sliding tests with EDTA PPP droplets were respectively performed on three SHP CNF/PTFE and CNF/PDMS Ti surfaces (15 mm by 7 mm) and fibrin fibre generation during the sliding test was confirmed using the setup in FIG. 5. After sliding test, the standard diluent from the kit was flushed over the surfaces using a pipette into reaction wells. As a control, the same procedures were performed on three pristine SHP CNF/PTFE Ti surfaces. Then, an ELISA test was performed following standard instructions. Optical density reading (450 nm) was used to calculate the fibrin concentration washed into the reaction wells from the tested SHP surface, with reference to the standard curve (fibrin concentration to optical density) acquired with porcine fibrin standard samples, to verify the existence of fibrin on the CNF surfaces after PPP sliding tests.

For testing static fibrin growth, forty microliters of EDTA PPP was dispensed onto a SHP CNF/PTFE Ti surface placed in a plastic petri dish and cultivated for 4 min at 37° C. The reaction was terminated by slowly adding sufficient DI water into the petri dish. The samples were then carefully rinsed by dipping into DI water three times. Samples were air-dried and fibrin structures grown on the surface were observed under SEM after gold coating.

For convenient observation of bacteria attached on the surface, a SHP CNF/PTFE coating was half-coated on a glass slide following the same procedure for the CNF/PTFE Ti surface. The SHP CNF/PTFE glass surface and the CNF/PTFE Ti surface were shown to have the same performance through water, blood, and PPP testing. Ten microliters of glycerol stock (50% glycerol, 50% cell culture in Luria-Bertani (LB)) of E. coli harbouring constitutive GFP expression plasmid stored at −80° C., was added into 3 ml fresh LB broth, supplemented with Kanamycin (Km) (50 μg ml$^{-1}$). The cells were incubated in a shaking incubator at 37° C. with a shaking speed of 225 r.p.m. The culture was diluted to OD$_{600}$ of 0.5 with fresh LB (50 μg ml$^{-1}$ Km). The CNF/PTFE glass slide sample was first sterilized with ultraviolet, then 40 μl cell culture was flushed over the sample surface across areas with and without CNF coating. The sample was subsequently air-dried in a biosafety cabinet for 20 min. Bacteria attached on the CNF surface were observed under a confocal laser scanning microscope, with laser wavelength of 473 nm for exciting the GFP.

To compare the clotting performance of the present CNF gauze, chitosan gauze was prepared by spray coating the chitosan and PDMS composite dispersion onto the pristine gauze. For fair comparison, weight ratio of chitosan to PDMS was 1:2, the same as CNF to PDMS weight ratio for the present CNF gauze. Twenty-five milligrams of chitosan (medium molecular weight, Sigma Aldrich) was first dissolved in 5 ml 0.15 M acetic acid with an ultrasonic probe; 50 mg PDMS (pre-polymer to cross linker weight ratio 9:1) was dispersed in 10 ml acetone by the ultrasonic probe. After mixing the two dispersions under ultrasonication for 5 min, the composite dispersion was spray-coated onto a pristine gauze (size: 10 cm by 10 cm) following the same protocol for preparing the CNF gauze. After coating, the chitosan gauze was baked at 80° C. for 1 h to evaporate the solvent.

The clotting test was performed using the citrated blood. Different types of gauzes were used—the SHP CNF gauze and the normal superhydrophilic gauze, in patches of 15 mm by 15 mm. These were pre-warmed in 20 ml polystyrene (PS) plastic petri dishes (37° C. water bath). After mixing the citrated blood with 0.2 M $CaCl_2$ at a volume ratio of 10:1 to initiate coagulation, 20 µl blood was immediately dispensed and sandwiched between two gauzes in the petri dish as shown in FIG. 15a—on the CNF gauze, blood was in contact with the surface coated with CNF. Blood dispensed in an empty petri dish without gauze was used as the control case, denoted as Control in FIG. 13d. Blood dispensed on different samples was allowed to coagulate at 37° C. for 0, 3, and 5 min, terminating coagulation by adding 10 ml DI water into the petri dish without disturbing the clot. Non-clotted red blood cells (free blood cells not trapped in the clot) would haemolyse and release haemoglobin into the water. Optical absorbance of the resulting haemoglobin solution at different clotting time t, HA(t), measured by the spectrophotometer at 540 nm, would represent the amount of haemoglobin from unclotted red blood cells. HA(0). The absolute haemoglobin absorbance of 20 µl blood in 10 ml DI water at t=0 min, was used as reference. RHA(t), the relative haemoglobin absorbance at clotting time t, was calculated as HA(t)/HA(0). This was averaged over three repetitions, n=3, using the same batch of blood. As the haemoglobin came from unclotted red blood cells, a smaller RHA(t) would mean faster clotting.

As for the nominal blood contact area (NCA) during the clotting test, following the same protocol, 20 µl blood was placed between two normal gauzes or two CNF gauzes for coagulation to occur. After 1 h, the two pieces of gauze were separated and a picture taken from the top was processed to calculate the NCA (averaged over three repetitions, n=3). NCA on the normal gauze was considered as the darkened area, which was soaked by blood, whereas NCA on the CNF gauze was considered as the clot-gauze contact area (FIG. 15b). In this test, the uncoated gauze absorbed blood quickly, leading to a large blood contact area, whereas the SHP CNF gauze repelled blood and its blood contact area was only 14.2±0.7% (mean±SD, n=3) of that on the uncoated pristine gauze (FIG. 15b). Following the same protocol, clotting performance of the present CNF gauze was further compared with the chitosan gauze with 50 µl blood (n=3), the results (FIG. 21) showing that the present CNF gauze can have better clotting performance than the chitosan gauze.

For determining clotting without blood loss: mimicking a wound dressed with a medical gauze, an opening representing the wound (8 mm by 5 mm) was made on a silicone tube (inner diameter: 7.8 mm) and was covered with the SHP CNF gauze by medical tape (FIG. 15c). A silicone tube dressed with the normal gauze was used as control. The citrated blood was mixed with $CaCl_2$ to initiate coagulation. Blood (1.5 ml) was quickly filled into the silicone tube and placed in a petri dish. After 10 min at room temperature, the tube was removed from the petri dish and the weight increase in petri dish due to blood leakage was measured as the blood loss. The test was repeated three times (n=3) to get the average blood loss.

To test the maximum pressure that the CNF gauze (without a back-supporting impervious membrane) could withstand before blood leakage, citrated blood was slowly filled into a long tube with a hole sealed by the CNF gauze (FIG. 15d). The height of blood column h, which was measured at the moment of blood droplets leaking through the CNF gauze, was used to calculate the maximum anti-leakage pressure P for a single layer of CNF gauze without the back-supporting impervious membrane (P=ρgh, where ρ is the blood density and g is the gravitational constant, averaged over three repetitions; n=3).

The anti-wetting property of the SHP CNF gauze with a back-supporting impervious membrane was further tested using the setup in FIG. 15e. A transparent PS petri dish was glued (epoxy glue) onto the back of the SHP CNF gauze as the impervious membrane. Glue was not applied at the central part of the gauze. Subsequently, the petri dish with the attached CNF gauze was placed in a transparent pressure chamber and filled with blood to completely immerse the CNF gauze (FIG. 15e). Citrated blood was used to ensure blood fluidity. Hydrostatic pressure applied on the CNF gauze surface was controlled by pumping air into the sealed pressure chamber with the assistance of a check valve and a pressure sensor. As the CNF gauze was placed 2-3 mm deep in the blood, the air pressure in the pressure chamber was taken as the hydrostatic pressure exerted onto the CNF gauze. A camera projecting upward was used to detect whether the central part of the CNF gauze was wetted by blood at a given pressure.

To test clot detachment, the SHP CNF Ti mesh and the SHP CNF gauze were placed in a 20 ml PS plastic petri dish pre-warmed at 37° C. (FIG. 15a). After mixing citrated blood with 0.2 M $CaCl_2$ at a volume ratio of 10:1 to initiate coagulation, 100 µl blood was immediately dispensed onto the CNF Ti mesh or the CNF gauze for the clot to form. After natural solidification and drying overnight, clots on the SHP CNF surfaces, before and after detachment, were coated with gold for SEM observation.

Figure 22:
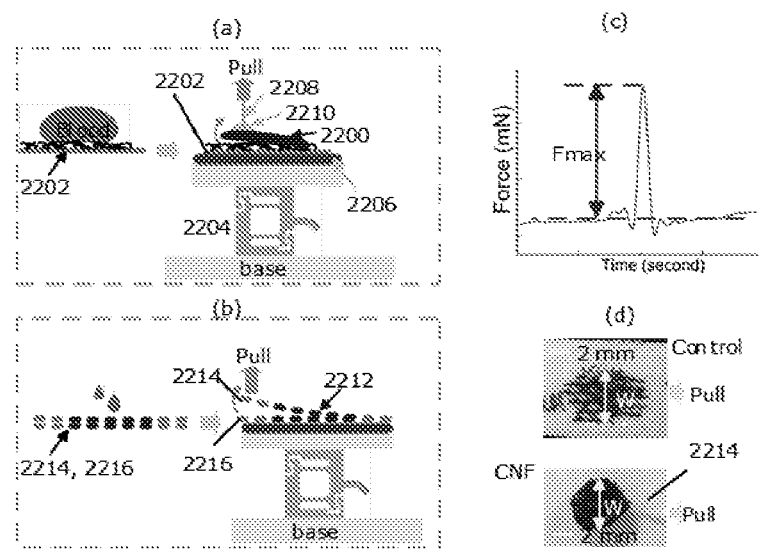

To detect clot peeling force, citrated blood was mixed with 0.2 M $CaCl_2$) at a volume ratio of 10:1 to trigger the coagulation. The blood clot was allowed to form and solidify overnight at 37° C. on the CNF gauze surface or between two pieces of uncoated gauze by dispensing 20 µl blood onto the CNF gauze surface or onto two stacked normal gauzes (FIG. 22). Using the setup in FIGS. 22a and 22b, the force required for peeling the clot from the CNF-coated gauze or the uncoated gauze was measured. FIG. 22a shows a clot 2200 formed by dispensing 20 µl blood onto the CNF gauze surface 2202. The gauze 2202 was mounted onto a strain gauge force transducer 2204 (capacity: 980 mN, resolution: 0.1 mN) by 3M high-strength tape 2206. A thin cotton 2208 wire was glued onto the clot 2200 by epoxy 2210. The force for peeling the clot 2200 was recorded by the force sensor 2204. FIG. 22b shows a clot 2212 formed between two normal gauzes 2214, 2216 by dispensing 20 µl blood. The force required to peel the two normal gauzes 2214, 2216 was measured while pulling the top gauze 2214. Pulling motion was performed with a homemade translation stage at 0.5 mm/s and the force data were recorded by a National Instruments multifunction data-acquisition device (NI USB-6218) controlled by Labview. FIG. 22c shows a typical clot peeling force curve, showing the maximum peeling force $F_{max}$. FIG. 22d provides the measurement of the clot maximum width W for the calculation of the clot peeling tension $F_{max}/W$. As the peak peeling force $F_{max}$ (FIG. 22c) would occur at the maximum clot width W, the normalized clot peeling tension $F_{max}/W$ (averaged over three repetitions) was used to compare the clot peeling force for the CNF gauze and the uncoated normal gauze.

For the in vivo test, CNF gauze and the normal uncoated gauze (used as control) were prepared to be plaster-like—FIGS. 21a and 21b (CNF gauze 2106 and normal gauze 2108). The gauze was cut to be 35 mm long and 15 mm wide, and was mounted onto a transparent adhesive tape (50 mm long and 25 mm wide). An opening (10 mm long and 5 mm wide) was made in the centre of adhesive tape, allowing blood to seep through the gauze in case of excessive bleeding. In FIG. 21a, for the design of the plaster-like gauze, the CNF gauze or the normal gauze 2100 (35 mm by 15 mm) was applied onto the adhesive film 2102 (50 mm by 25 mm), and the opening 2104 was made on the adhesive film 2102 to allow blood to seep through in case of excessive bleeding. Prepared CNF gauze and normal gauze were sterilized under UV for 30 min before experiment.

For the in vivo experiments, female rats 2110 (Sprague-Dawley, 11-13 weeks old, average body weight: 255.6±19.7 g, mean±SD) were used, complying with all relevant ethical regulations for animal testing and research. Rats were anaesthetized by isofluorane (4-5% in 100% oxygen for induction and 1-3% for maintenance) with a thermal pad to prevent hypothermia. Hair on the back was first shaved with an electric razor. Residual hair was removed with hair removal cream. Surgical instruments were autoclaved. The experiment was performed in the biological safety cabinet using aseptic techniques. The operative site on back of the rat was disinfected with iodine and 70% v/v ethanol successively for three times. Two incisions 2112 (about 1 cm long; cut down to muscle) were made on the back of the rat, one on the left and one on the right at the same position. Upon incision, the plaster-like gauze was applied onto the wound instantly (FIGS. 21c and 21d).

Blood loss was characterized by measuring the weight increase in gauze. Weight of the gauze peeled at 3 min (FIG. 21e) minus its initial weight was taken as the blood loss. Gauze weight was measured by a high-precision weighing balance (resolution: 1 mg). The data were averaged over six repetitions.

The peeling force was measured by peeling the gauze along the wound after about 2 h (132±10 min and 133±10 min for the control and the CNF gauze, respectively; mean±SD, n=5), allowing the clot to sufficiently mature and solidify. Before gauze peeling, the adhesive film around the gauze was carefully trimmed away, otherwise the adhesive film taped on skin would interfere with the peeling force. With reference to FIG. 21g, in the absence of trimming the adhesive film (2114) taped onto skin would interfere with the peeling force. Care was taken not to stretch or tear the gauze during the trimming. After adhesive film trimming, one end of the gauze was adhered onto a metal hook 2116 by high-strength tape 2118, which was attached onto a force sensor (capacity: 980 mN; resolution: 0.1 mN) by a thin cotton wire 2120—see FIG. 21h. Peeling was assisted by a vertical numerical translation stage and the peeling force was recorded. The maximum force during peeling, averaged over five measurements see FIG. 21i, was used for a quantitative comparison.

Figure 25:
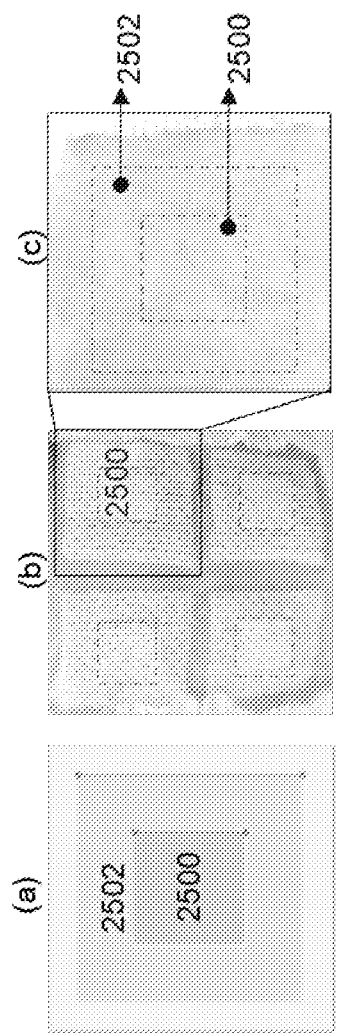

The skin compatibility test was also conducted in vivo by attaching the present material onto rat skin for 12 h (see FIG. 25). Preparation of the samples used for the skin compatibility test is illustrated in FIG. 25a, with a 10 mm by 10 mm CNF sample 2500 attached onto a 20 mm by 20 mm pristine gauze 2502. This design permitted comparison of two adjacent skin areas contacted with different gauze materials. Before testing, rats were anesthetized and shaved. Prepared samples were then applied on rat skin of three rats, with transparent clinical tape for 12 h (see FIG. 25b). To prevent samples from being scratched off by rats, rat jackets were used to protect the gauze samples. After 12 h, rats were anesthetized to remove the gauze. The tested skin area was gently cleaned with 70% v/v ethanol to examine any difference between the areas under the present CNF gauze and the pristine gauze (see FIG. 25c)—no difference was observed.

It will be appreciated that many further modifications and permutations of various aspects of the described embodiments are possible. Accordingly, the described aspects are intended to embrace all such alterations, modifications, and variations that fall within the spirit and scope of the appended claims.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A haemostatic device comprising:
a substrate; and
a surface formed on the substrate, the surface comprising at least one of micro- and nano-sized materials, the materials being partially embedded in a base, the surface substantially preventing wetting of the substrate, wherein the materials comprise hydrophobic nanofibers immobilized in the base, wherein the surface has a surface morphology that entrains air pockets between the surface and a liquid coming into contact with the surface.

2. The haemostatic device of claim 1, wherein the nanofibers are carbon nanofibers.

3. The haemostatic device of claim 1, wherein the surface morphology is a random surface morphology to obtain a water contact angle of at least 130°.

4. The haemostatic device of claim 1, wherein the surface, once formed, has a random surface morphology of one of micro-roughness and nano-roughness.

5. The haemostatic device of claim 1, wherein the nanofibers have a diameter of about 5-1000 nm and/or a length of about 5 to 500 μm.

6. The haemostatic device of claim 1, wherein the base is hydrophobic.

7. The haemostatic device of claim 6, wherein the base is an organic or polymeric matrix.

8. The haemostatic device of claim 7, wherein the matrix is a biocompatible polymer capable of immobilizing the materials.

9. The haemostatic device of claim 8, wherein the biocompatible polymer is at least one of polytetrafluoroethylene (PTFE), beeswax and polydimethylsiloxane (PDMS).

10. The haemostatic device of claim 1, being one of a wound dressing, catheter-based stent, coil or graft.

11. A haemostatic coating dispersion comprising at least one of micro- and nano-sized materials, and a base in a dispersion, for depositing on a substrate to form a hydrophobic surface comprising the materials partially embedded in the base, the surface substantially preventing wetting of the substrate, wherein the materials, when at least partially embedded, are hydrophobic, and the materials comprise nanofibers immobilized in the base on formation of the hydrophobic surface, wherein the surface has a surface morphology that entrains air pockets between the surface and a liquid coming into contact with the surface.

12. The haemostatic coating dispersion of claim 11, wherein the nanofibers are carbon nanofibers.

13. The haemostatic coating dispersion of claim 11, wherein the surface morphology of the surface, once formed, is a random surface morphology of one of micro-roughness and nano-roughness.

14. The haemostatic coating dispersion of claim 11, wherein the materials comprise nanofibers having a diameter ranging from about 5 nm to 1 micron or micro-sized materials having a diameter from about 1 μm to 200 μm.

15. The haemostatic coating dispersion of claim 14, wherein the materials have a length of about 5 to 500 μm.

16. The haemostatic coating dispersion of claim 11, wherein the base is an organic or polymeric matrix.

17. The haemostatic coating dispersion of claim 16, wherein the matrix is at least one of polytetrafluoroethylene (PTFE) and polydimethylsiloxane (PDMS), or other biocompatible polymers capable of immobilizing the nanofibers.

18. A hydrophobic surface formed by applying the haemostatic coating dispersion of claim 11 to a substrate.

* * * * *